(12) United States Patent
Gómez-Elvira Rodríguez et al.

(10) Patent No.: US 8,097,209 B2
(45) Date of Patent: Jan. 17, 2012

(54) METHOD AND APPARATUS FOR DETECTING SUBSTANCES OR ANALYTES FROM THE ANALYSIS OF ONE OR MORE SAMPLES

(75) Inventors: Javier Gómez-Elvira Rodríguez, Madrid (ES); Eduardo Sebastián Martínez, Madrid (ES); Carlos Briones Llorente, Madrid (ES); Victor Parro García, Madrid (ES); José Antonio Rodríguez Manfredi, Madrid (ES); Carlos Compostizo Sañudo, Vizcaya (ES); Pedro Luis Herrero Gonzalo, Vizcaya (ES); Juan Pérez Mercader, Madrid (ES)

(73) Assignees: Instituto Nacional de Technica Aerospacial "Easteban Terradas", Madrid (ES); Sener, Ingenieria Sistemas, S.A., Vizcaya (ES); Consejo Superior de Investigaciones Cientificas, Madrid (ES)

( * ) Notice: Subject to any disclaimer, the term of this patent is extended or adjusted under 35 U.S.C. 154(b) by 1161 days.

(21) Appl. No.: 10/558,936

(22) PCT Filed: May 28, 2004

(86) PCT No.: PCT/ES2004/000244
§ 371 (c)(1),
(2), (4) Date: Dec. 18, 2006

(87) PCT Pub. No.: WO2004/106922
PCT Pub. Date: Dec. 9, 2004

(65) Prior Publication Data
US 2007/0099189 A1    May 3, 2007

(30) Foreign Application Priority Data
May 30, 2003    (ES) .................................. 200301292

(51) Int. Cl.
*C12Q 1/68* (2006.01)
(52) U.S. Cl. ........................................................ 422/50
(58) Field of Classification Search .................. None
See application file for complete search history.

(56) References Cited

U.S. PATENT DOCUMENTS

| | | | | |
|---|---|---|---|---|
| 5,605,841 | A * | 2/1997 | Johnsen et al. | 436/164 |
| 5,759,847 | A * | 6/1998 | Eden et al. | 435/286.4 |
| 5,925,522 | A | 7/1999 | Wong et al. | |
| 6,431,476 | B1 | 8/2002 | Taylor et al. | |
| 6,905,816 | B2 * | 6/2005 | Jacobs et al. | 435/5 |
| 6,994,827 | B2 * | 2/2006 | Safir et al. | 422/130 |
| 7,118,907 | B2 * | 10/2006 | Williams et al. | 435/287.1 |
| 2002/0197631 | A1 * | 12/2002 | Lawrence et al. | 435/6 |
| 2003/0040976 | A1 | 2/2003 | Adler et al. | |

FOREIGN PATENT DOCUMENTS

| | | |
|---|---|---|
| EP | 1 179 585 A2 | 2/2002 |
| ES | 2 169 770 | 7/2002 |
| WO | 97/00726 | 1/1997 |
| WO | 00/16903 | 3/2000 |

OTHER PUBLICATIONS

Collins et al. "A branched DNA signal amplification assay for quantification of nucleic acid targets below 100 molecules/ml." *Nucleic Acids Research*. vol. 25. No. 15. 1997. pp. 2979-2984.
Fojta et al. "Supercoiled DNA-modified mercury electrode: A highly sensitive tool for the detection of DNA damage." *Analytica Chimica Acta*. vol. 342. 1997. pp. 1-12.
Gingeras et al. "Simultaneous Genotyping and Species Identification Using Hybridization Pattern Recognition Analysis of Generic *Mycobacterium* DNA? Arrays." *Genome Res*. vol. 8. 1998. pp. 435-448.
Hacia et al. "Determination of ancestral alleles for human single-nucleotide polymorphisms using high-density oligonucleotide arrays." *Nature Genetics*. vol. 22. 1999. pp. 164-167.
Karube. "Proceedings of the Annual Conference on Engineering in Medicine and Biology." *IEEE*. 1990. pp. 5-6—Abstract only.
Marco. "Immunochemical techniques for environmental analysis. II. Antibody production and immunoassay development." *Trends in Analytical Chem*. vol. 14. No. 8. 1995. pp. 415-425.
Marko-Varga. "Development of enzyme-based amperometric sensors for the determination of phenolic compounds." *Trends in Analytical Chem*. vol. 14. No. 7. 1995. pp. 319-328.
Mulchandani et al. "Fiber-optic enzyme biosensor for direct determination of organophosphate nerve agents." *Biotechnol. Prog*. vol. 15. 1995. pp. 130-134.
Reidel et al. "Rapid physiological characterization of microorganisms by biosensor technique." *Microbiol. Res*. vol. 152. No. 3. 1997. pp. 233-237.—Abstract Only.

(Continued)

*Primary Examiner* — Ann Lam
(74) *Attorney, Agent, or Firm* — Merchant & Gould P.C.

(57) ABSTRACT

The invention relates to a method and apparatus for detecting substances or analytes form the analysis of one or several samples. The method comprises mixing the sample with a suitable liquid buffer, homogenizing said sample, adding reagents thereto, filtering it, injecting the sample into the incubation chamber, allowing the sample to react with a biosensor, washing the non-reacted sample excess and detecting the sample retained in the biosensor. The apparatus includes a sample homogenizer module with an ultrasonic piezoelectric device formed by a converter (49) and a horn (16); a sample processing module including a homogenization container (6) and a moving frame (17); a reagent and solution management module including a motorized syringe (60), a reaction module consisting of a support (50) forming a reaction chamber (51) and a data reading module including a laser diode (66) and a CCD camera (67).

24 Claims, 12 Drawing Sheets

OTHER PUBLICATIONS

Southern et al. "Arrays of complementary oligonucleotides for analyzing the hybridization behavior of nucleic acids." *Nucleic Acids Res.* vol. 22. No. 8. 1994. pp. 1368-1373.

Southern et al. "Molecular interactions on microarrays" *Nature Genetics Supplement.* vol. 21. 1999. pp. 5-9.

Stuyver et al. "Line Probe Assay for Rapid Detection of Drug-Selected Mutations in the Human Immunodeficiency Virus Type 1 Reverse Transcriptase Gene." *Antimicrobl Agents and Chem.* vol. 41. No. 2. 1997. pp. 284-291.

Van Emon et al. "Immunochemical Methods for Environmental Analysis." *Anal. Chem.* vol. 64. No. 2. 1992. pp. 79-88.

Wang et al. "Remote electrochemical biosenseor for field monitoring of phenolic compounds." *Anal. Chem. Acta.* vol. 312. 1995. pp. 39-44.

Cheng et al. "A piezoelectric quartz crystal sensor for the determination of coagulation time in plasma and whole blood." *Biosensors & Bioelec.* vol. 13. No. 2. 1998. pp. 147-156.

\* cited by examiner

METHOD AND APPARATUS FOR DETECTING SUBSTANCES OR ANALYTES FROM THE ANALYSIS OF ONE OR MORE SAMPLES

The present invention refers to an apparatus for detecting substances or analytes from the analysis of one or more samples, which allows carrying out the analysis of a large number of samples at the same time and which can further be operated by remote control. The invention also includes the method for detecting said substances or analytes.

The development of biosensors, i.e. detection systems based on the molecular properties of living beings, has constituted a real biotechnological revolution in recent years, since it allows assessing the existence of certain substances in a medium, and analyzing its features (amongst these, its possible toxicity or pathogenicity).

Environmental biosensors are based on the use of biological recognition systems coupled to signal transducers. There are three basic mechanisms of biological recognition: biocatalysis, bioaffinity and metabolic. Likewise, transduction systems may be electrochemical, optical-electronic, optical or acoustic. Catalytic transformation of a substance (for example, a polluting compound) in a detectable manner with a sensor or by inhibition of an enzyme by said substance, are the two basic operating mechanisms of biosensors based on biocatalysis. Examples of the first of these constitute the use of tyrosinase for detecting phenols (Chen W. J., 1995; Marko-Varga et al., 1995), or the use of organophosphate hydrolase for detecting organophosphate pesticides (Mulchandani et al., 2000).

Amongst the limitations inherent to these systems are the reduced number of pollutants which are substrates of known enzymes, the need for relatively high concentrations of the pollutant for it to be detected, the presence of inhibitors in the medium, the need for using additional substrates, cofactors or mediators, developing reagents, etc. Furthermore, the irreversible nature of many enzyme-substrate interactions means that the biosensor cannot be reused.

The highly specific reactions of the antibodies with their antigens, or of hybridization between complementary nucleic acids, constitute the most used bioaffinity systems. The first bioaffinity biosensors with environmental applications were based on the use of antibodies due to the availability of monoclonal and polyclonal antibodies against a large amount of polluting substances (Van Emon and López-Avila, 1992; Marco et al., 1995), such that immunosensors constitute the most used type of biosensor for environmental purposes. There is amongst the immunosensors a wide range of commercial formats and kits (both reusable and single-use) which allow dealing with aspects as important as multifunctionality, format versatility, test time, sensibility, costs, reproducibility, conservation, etc.

The development of biosensors based on affinity reactions between nucleic acids (specific hybridization) for environmental applications has only just begun. Examples of applications of this type of biosensors are detecting DNA damage produced by chemical agents (Fojta and Palecek, 1997) or detecting microorganisms by using species-specific DNA probes (Cheng et al., 1998). The company PE Biosystems (www.pebiosystems.com) markets kits for detecting and identifying bacteria based on the amplification and sequencing of a universal gene, the gene coding for 16S ribosome RNA.

There are also different types of biosensors in the field of biomedicine based on antigen-antibody reaction or on the specific hybridization of nucleic acids for the detection and quantification of pathogenic microorganisms. Immunoassay detection techniques have been developed, in different formats, for detecting bacterial and viral pathogens. The most refined variants of these techniques allow even quantifying the pathogen existing in a body fluid, such as the quantitative LCx-RNA techniques developed by Abbott (www.abbottdiagnostics.com). As examples of methodologies based on nucleic acid hybridization, several variants of ranched-DNA techniques, marketed by Roche (www.roche-diagnostics.com) are mentioned, which allow the direct quantification of pathogenic viruses in the blood stream, among them the human immunodeficiency virus or the hepatitis B or C viruses (Collins et al, 1997). Differential microorganism genome hybridization with nucleic acid probes immobilized on nitrocellulose strips (LiPA techniques marketed by Abbott) allows conducting viral strain or variant genotyping (Stuyver et al. 1997).

Another biological recognition system is based on the study of the microbial metabolism. Therefore, the measurement of the increased concentration of a compound according to cellular respiration, or the inhibition of respiration by said compound, and the specific recognition of gene expression promoters or regulators on the part of the compound, are examples of this type of biosensors (Karube, 1990; Riedel, 1998). Microorganisms genetically modified by means of transformation with plasmids carrying reporter genes (luciferase, beta-galactosidase, etc) under the control of a promoter recognized by the analyte of interest, recognizing and detecting the presence of environmental contaminants, have been developed.

The recent development of DNA microarray technology, also called DNA chips or microchips (Southern et al., 1994; for a review see Nature Genetics 21, supplement, 1999), allows covalently fixing thousands of molecular probes (nucleic acids, proteins, carbohydrates, etc.) to a solid carrier (glass, nitrocellulose, nylon, etc.), thus constituting a considerable advancement both in the scaling and in the possibility of developing bioaffinity biosensors.

DNA chips can mainly be applied to gene expression, genome resequencing and genotyping studies. It is possible to analyze the expression at the RNA level of thousands of genes from samples of diseased tissue (cancer, infected by virus, bacteria, fungi, etc.) or of the infectious agents themselves (Cheng et al., 1998). The discovery of the genes involved in these processes allows finding and designing new drugs, new diagnosis methods, etc. Resequencing and genotyping studies allow discovering nucleotide mutations and polymorphisms (SNPs) in the studied organisms (Hacia et al., 1999).

Another field of application of DNA chips is in the identification of microorganism species, mainly the variants or strains (more or less virulent) of the same species (Gingeras et al., 1998), either for clinical purposes (resistance to drugs, toxins, pathogenicity factors, etc.) or for ecological purposes (biodiversity, polymorphic dispersion, etc.). Gingeras et al. constructed a DNA chip with oligonucleotides interrogating all the positions (in both chains) of a 75 bp DNA fragment of the *Mycobacterium tuberculosis* rpoB gene so as to analyze the existence of mutations conferring resistance to rifampicin in a collection of 63 clinical isolates of *M. tuberculosis*. Species identification is based on the existence of species-specific polymorphisms that can be easily determined with a DNA microchip. Another example of the use of DNA chips for identifying bacteria is U.S. Pat. No. 5,925,522, in which Wong et al. (1999) describe methods for detecting *Salmonella* by means of DNA chips with specific oligonucleotide sequences.

One of the main problems at the time of analyzing the presence of substances in a medium is that these substances are, in most cases, very diluted, making it necessary to use large starting volumes. For example, infectious gram-negative bacteria can be present in less than 10 copies per milliliter (ml) of blood or of potable water, viruses such as the human immunodeficiency virus can exist in less than 5 copies/ml of blood in an infected patient, and infectious agents such as *Escherichia coli* and *Salmonella* can manifest themselves is less than 10 copies/gram of food. European patent EP 1 179 585, A3 (publication date of 13 Feb. 2002) provides a solution to the problem of applying large volumes to analysis systems based on microfluidics by means of the incorporation of microfluidics chips or components in larger cartridges containing any combination of detection and processing channels, chambers, reservoirs or regions. Said invention describes a utensil for separating analytes from a fluid and concentrating them in a volume that is less than the original volume. Said analytes can be from organisms, cells, proteins, nucleic acids, carbohydrates, viral particles, chemical or biochemical compounds, though the preferred use is for detecting nucleic acids.

From the foregoing, it is evident that the capability of measuring contaminants or pathogens in the air, water and soil is crucial for understanding and evaluating the risks of the presence of said analytes on human health and the ecosystem. The costs inherent to analytical chemistry are becoming increasingly higher, and as a response considerable advancements have been made both in laboratory detection methods and in analytical field techniques, where sampling and analysis are done in situ. Transport of samples, with all that this entails, i.e. packaging, transport, storage and care, etc., is reduced with the incorporation of field techniques and decision-making is facilitated. On the other hand, in situ techniques allow a significant reduction in the time comprised between the sampling and analysis, so the risk of (chemical, photochemical or thermal) degradation or contamination thereof is considerably reduced. Nevertheless, and even though they are relatively fast and inexpensive methods, they have certain limitations such as the capability of analyzing a narrow range of compounds and a sensitivity and precision that are inferior to classic laboratory techniques. However, they allow taking a large number of samples in contaminated sites, and they are particularly important for integral study plans in certain areas where continual follow-up is indispensable. The methods used must anticipate the presence of unexpected pollutants or pathogens, even at very small concentrations, which however may be extremely hazardous.

The characterization of contaminated areas must be carried out by means of a combination of analytical laboratory methods and in situ diagnostic and tracking methods. Once a key marker is identified, field methods allow mapping its spatial and temporal distribution, as well as to perform a precise follow-up throughout a possible remediation process. A wide variety of laboratory techniques based on biosensors have been described, and many of them already marketed, for detecting and measuring the concentration of biomarkers in a medium or an organism. A large number of such techniques are carried out by instruments in a semi-automatic and a robotized manner. Apart from their complexity, large size and high economic cost, such instruments must compete with other field methods, such as immunoassays, chemical test kits, and other miniaturized laboratory techniques, besides the marketing obstacles common to this type of such highly specialized products. There are currently several pieces of portable equipment for in situ analyte detection, but they require trained professionals to handle them. Therefore, a good biosensor instrument must be versatile enough to measure several elements and within a wide range of concentrations, have a small size, and be able to detect complex chemical compounds automatically, continuously and by remote control. Equipment of these features are those indicated for continuous monitoring of analytes in fixed stations of rivers, seas, lakes, etc., or for being incorporated in a moving system (for example a robot) that allows analyzing samples in different points of soils or aquatic mediums.

The detection of contaminating (toxic or not) substances (analytes) in a medium or organism is extremely important when making decisions of both an environmental and a medical nature. In many cases, an isolated analysis is enough, but many times continuous monitoring of one or several analytes is indispensable. To that end, the process must be repeated as many times necessary by a trained operator, with the subsequent costs in resources (economical, time, and duly trained staff), apart from the fact that the results may be compromised due to a lack of uniformity in said process. This problem is usually solved by means of automatic or semiautomatic sampling and analysis systems with complicated and sophisticated biomedical instruments or complex environmental follow-up stations. Furthermore, the number of substances analyzed simultaneously by means of the current methods is very low, or even of a single analyte in most cases. For example, the current most widely used methods for the microbiological analysis of waters, soils and buildings are based on classic culture techniques, on immunological assays, or more recently on PCR reaction, either with portable equipment or in a laboratory, but always with a limited number of samples and analytes. On the other hand, there are special situations in which sampling and analysis in situ is particularly difficult, such as in difficult access areas or in sites that are highly contaminated with toxic or biological products.

The present invention has as an object eliminating the drawbacks set forth by means of the development of a robotized apparatus susceptible to operation by remote control and a method allowing the analysis of multiple natural samples, and the simultaneous detection and characterization from dozens to thousands of different analytes in a single assay. The present invention benefits from the recent development of protein and DNA microarray technology, which has remarkably increased the analysis capacity and detection sensitivity, allowing the study of biological, biomedical and biosanitary problems. Unlike the technologies based on microarrays that have been developed up until now (which require specialized staff and complex and tedious protocols for processing the samples), the treatment of the sample to be analyzed is considerably reduced and the entire process is robotically carried out in the present invention.

The invention includes an apparatus capable of processing volumes ranging from nanoliters to milliliters of a liquid sample (body fluids, water), or a suspension (of soil, sediment or previously crushed rock); and a method allowing the detection of at least one analyte in a simple manner and without needing to purify or concentrate said sample.

The apparatus comprises a series of operative modules in which the samples are handled, treated and analyzed, and a series of control modules, for the operative modules, supervising the working of said operative modules. The working of the entire assembly is supervised by an overall control module. The apparatus further has a communications module.

More specifically, the apparatus of the invention consists of:
  a sample homogenizer module
  a sample processing module
  a reagent and solution management module a reaction module a data reading module The apparatus of the invention may further include a sample acquisition module and a sample distribution module.

In reference to the communication and control modules, they shall include:

a communications module an overall control module a sample acquisition control module a sample distribution control module a sample homogenizer control module a processing and reaction control module a reagent and solution management control module a data reader control module The sequence of processes that will be carried out with the apparatus and the method of the invention is:

1. Extraction of the sample to be analyzed through a sample acquisition module. Said samples can be in a liquid or solid state or in suspension.

2. The samples are distributed by means of a sample distribution module to the homogenization and processing position.

3. Prior to homogenization, a solution or suspension is prepared with the content of said samples. To that end, a reagent and solution management module controls the addition of a saline solution or a buffer solution so that it mixes with said sample.

4. Sample homogenization consists of forming a homogenous mixture of said sample and the saline or buffer solution for the purpose of maximally disintegrating the particulate material and dissolving the analytes present. This process is carried out by the sample homogenizer module.

5. The homogenized sample can be subjected to different processes in the sample processing module: chemical, biochemical or biological (it interacts with a live cell) modification, or a physical modification such as filtering, concentration, etc. The result of the processing may be molecular labeling or not of the analytes present in the sample. Said labeling may be formed by a fluorescent substance or any other substance allowing the subsequent identification of the modified analyte.

6. The processed sample circulates through the reaction module where it comes into contact with a sensing device. Said sensor is made up of one or more substances capable of interacting with the analytes (modified or not) present in the sample, such that said analytes are retained in the reaction module, while the sample excess is stored in a waste deposit.

7. Once the entire sample has circulated through the reaction module, said module may be washed with a solution controlled by the reagent and solution management module so as to remove processed sample residue. This washing operation may be eliminated and new reagents added to the reaction module and later perform new washings, if needed.

8. The final objective is the detection of analytes retained in the reaction module sensor. To that end, the data reading module is provided with devices detecting those labeled analytes (fluorescent or not). If said analytes have been modified with a fluorescent substance (fluorochrome), the reading module will be provided with a strong radiation to excite said fluorochrome, and a fluorescence detector.

9. The detected data is processed by suitable software for a final presentation of the result. Said presentation can consist of a bit map generating an image that can be processed by a computer, either by the data reading module software or by a remote station.

10. The final result of the process is sent to as remote station through the communications module.

The main advantages provided by the present invention with respect to current systems are:

1. Potential of automating the complete system, from sampling, processing and analysis to data transmission.

2. Considerable simplification of the number of steps necessary for processing the samples 3. Potential of miniaturizing 4. Capacity to detect in a single run from a few up to thousands of substances, preferably compounds of a biological origin.

5. Low energetic demands

6. Great independence

7. Possibility of remote control.

8. Possibility of application to planetary exploration (for example Mars)

A detailed description of each one of the modules forming the invention shall be given below.

In summary, the method of the invention for detecting substances or analytes from the analysis of one or more samples comprises the steps of: a) mixing said sample with a suitable liquid buffer; b) homogenizing with a homogenizing system; c) adding reagents to modify said sample; d) filtering the sample; e) injecting said sample in a reaction chamber; f) allowing the sample to react with a biosensor; g) washing the non-reacted sample excess; and h) detecting the sample retained in the biosensor. The different steps will be carried out following a command that may vary and will depend on the type of sample to be analyzed.

1.—Communications Module

The communications module is the equipment's interface with the user, who may be either local or remote. If the user is local, the communications module will allow establishing a connection according to any of the following protocols:

1. Console in the case of a local user.

2. Link via RS232, RS422 or RS485 series.

3. Parallel link.

4. USB (Universal Serial Bus) link.

5. TCP, UDP, or IP link, or any other protocol for data transmission between computers.

6. Radio, IRDA links . . .

7. Field buses: PROFIBUS, CAN, FieldBus, InterBUS-S, . . .

8. Telephone links: GSM,

In the case of the data link establishment, the communications module carries out data coding, encapsulation, control of access to the medium, sending/receiving data/commands and implementing safety options by means of the validation of all the commands.

2.—Overall Controller

This is the module controlling and supervising the working of all the equipment and carries out at least the following functions:

1. Receiving messages from the communications module; validating the parameters and commands received; interpreting such commands (tasks) sent by the user.

2. Task execution system: overall sub-process sequencing, sending commands to the corresponding local controllers.

3. Carrying out preprogrammed automatic tasks.

4. Supervising the working of each module: carrying out subtasks and safety verifications (monitoring the process parameters and checking their inclusion in the corresponding suitable working ranges). Emergency stop control if safety so requires this.

5. Recovery from subsystem failures.

6. Sending the working parameter values to the operator for their general process monitoring through the communications module.

This controller further allows both the local and remote operation of the apparatus.

3.—Sample Acquisition Module

The "sample acquisition module" is defined as the module that allows extracting, storing and transporting the samples to be analyzed in a robotized manner; these samples may be solids, liquids or in suspension.

The sample acquisition module consists of two parts: a device for extracting the sample and another one for the storage and transport thereof to the feed hopper.

The following particular embodiments are identified:

1. In a particular embodiment of the invention, the module has a robot for extracting solid samples with at least six degrees of freedom with a tool located on its distal end allowing the drilling of the soil or rock by means of a striker that is actuated by a hydraulic, pneumatic or mechanical system when it is working at frequencies between 1 Hz and 1 KHz, and actuated by a piezoelectric actuator for frequencies up to 60 KHz. The transport of the pulverized solid is carried out by means of a pneumatic aspiration and transport system.

2. In another particular embodiment of the invention, a hydraulic pumping system depositing the liquid sample in the hopper is used for extracting liquid samples.

3. In another particular embodiment of the invention, the module has a suction and filtering system for extracting samples in suspension (in air). The filter with the retained particles transfers part of the liquid to the sample distribution module.

4. In another particular embodiment of the invention, a suction system takes air from the medium surrounding the invention and the gas obtained is pumped into a solution, then a pump transfers part of the liquid to the sample distribution module.

4.—Sample Acquisition Controller

The sample acquisition controller is responsible for controlling all the mechanisms responsible for carrying out the functions described in section 3.

The sample acquisition control module will be actuated by the overall control module, will carry out the preprogrammed functions and will send an electrical, analog or digital signal to the overall control module when its function has concluded, the same as when an error in its execution has been detected.

In the particular embodiment of the sample acquisition module identified in point 1 of section 3, the sample acquisition control module will carry out the control of the articulated arm, as well as of the tool it is provided with for making holes in the soil, rocks, . . . and of the device used for collecting the pulverized samples.

In the particular embodiment of the sample acquisition module identified in point 2 of section 3, the sample acquisition control module will control the pump responsible for collecting the liquid samples.

In the particular embodiment of the sample acquisition module identified in point 3 of section 3, the sample acquisition control module will control the air suction system and the mechanism transferring the filter to the sample distribution module.

In the particular embodiment of the sample acquisition module identified in point 4 of section 3, the sample acquisition control module will control the air suction system and the pump taking the liquid sample from the deposit where the air has been pumped and deposits it in the sample distribution module.

5.—Sample Distribution Module

"Sample distribution module" is defined as the group of devices allowing the independent analysis of several samples taken with the same sample acquisition module, so it requires a mechanism for distributing the samples from the feed hopper to the different sample processing module homogenization containers.

In a particular embodiment, the sample distribution module is provided with a moving device, for example in the form of a rotating drum, capable of housing one or more homogenization containers, which allows placing the container that is to be used under the feed hopper for receiving the solid or liquid sample, or a filter with retained particles in suspension. Once the sample is introduced in the homogenization chamber, the drum rotates again until placing the container in alignment with the sample processing module moving rack so as to initiate sample processing.

The moving device or rotating drum may be assembled on a vertical or horizontal shaft with the ability to rotate thereon.

6.—Sample Distribution Controller

The sample distribution controller is responsible for controlling the mechanisms, sensors and electromechanical actuators for suitably distributing the samples introduced in the sample distribution module.

The sample distribution control module will be actuated by the overall control module, will carry out the preprogrammed functions and will send an electrical, analog or digital signal to the overall control module when its function has concluded, the same as when an error in its execution has been detected.

In the particular embodiment indicated in section 5, it is responsible for controlling the motor rotating the rotating drum using the corresponding sensors to identify the drum position.

7.—Sample Homogenizer Module

The sample homogenizer module is made up of a device capable of acting on the samples to produce their homogenization. Said device can be of mechanical action, such as grinders and vibrating devices, of thermal action (resistors, etc.), or wave generating devices (ultrasounds, etc.). Said devices are capable of regulating the degree of stirring and homogenization of said samples, from a gentle mixing to causing the breaking of cells (lysis) that are as resistant as the spores of some microorganisms.

The following particular embodiments of the sample homogenizer module have been identified:

1. In a particular embodiment of the invention, the sample homogenizer module is formed by an ultrasound generating piezoelectric device converting high frequency electrical power supplied by the homogenizer controller into longitudinal vibrations. Such vibrations are amplified through the free end of a horn, firmly attached to the piezoelectric device. The sample homogenizer module is housed inside the rack closing the main sample processing module chamber, firmly fixed to it and in contact with the wall closing said chamber.

The vibrations from the horn generate pressure waves in the solution or suspension containing the processed sample which in turn cause cavitation in said solution or suspension, disintegrating the particulate material and lysing the cells that may exist in the sample and thus homogenizing said sample. The lysing can be improved by introducing microspheres in the liquid sample.

Ultrasonic lysing can be carried out by means of the direct action of the horn in the liquid or through a membrane as is carried out in U.S. Pat. No. 6,431,476.

The sample processing module pressure and temperature sensors monitor the proper working of the process.

2. In another particular embodiment of the invention, the sample homogenizer module is formed by a mechanical blade or piston homogenizer. The mechanical action of the blades or the piston in the liquid and the friction with the walls allows homogenization and even lysing. The improvement of the homogenization is possible by adding abrasive agents.

8.—Sample Homogenizer Controller

The sample homogenizer controller is responsible for controlling the electromechanical mechanisms and sensors necessary for suitably homogenizing the samples introduced in the sample homogenizer module.

The sample homogenizer control module will be actuated by the overall control module, will carry out the preprogrammed functions and will send an electrical, analog or digital signal to the overall control module when its function has concluded, the same as when an error in its execution has been detected.

In the particular embodiment 1 of point 7, the sample homogenizer control module converts the electrical power from the supply system into high frequency electrical power, transmitting it to the piezoelectric device according to the pre-established time sequence. It further regulates the output voltage to the piezoelectric device by modifying the amplitude in the vibration.

In the particular embodiment 2 of section 7 of the sample homogenizer control module, the electromechanical device operating the blades or the piston must be activated/deactivated.

9.—Sample Processing Module

The "sample processing module" is defined as an assembly of devices the purpose of which is to subject said samples to different physical treatments (homogenization, lysis, heating, radiation, etc.), chemical treatments (modification with chemical or biochemical agents such as enzymatic reactions, etc.), or biological treatments (interaction with microorganisms).

In a particular embodiment of the invention the sample processing module is provided with two clearly differentiated subassemblies: a homogenization container housing the sample inside the homogenization chamber, and a moving rack closing said chamber.

In a particular embodiment of the invention, the sample processing module includes from one to several homogenization containers, allowing the analysis of at least one sample per container. Each homogenization container is provided with one or more main homogenization chambers surrounded by several secondary chambers connected with it by means of conduits of different sizes. The main homogenization chamber is open so as to receive the samples in the solid or liquid state through the sample acquisition module hopper. During processing of the sample, this opening is hermetically sealed by the piston of the rack closing the sample processing module. The secondary chambers of the homogenization container are hermetically sealed with silicon caps and communicated with the main chamber by means of conduits of various section sizes. These secondary chambers are used for introducing several reagents into the homogenization chamber, injected by means of the reagent and solution management module cannulas. Several of these secondary chambers house probes to measure parameters of the processes carried out in the main homogenization chamber (temperature, pressure, pH, conductivity, etc.).

The wall of the main chamber has a venting port, determining the moment of hermetic sealing of said chamber by the piston, as said port is surpassed by the piston, for example by a leak-tight ring joint of said piston. This piston can furthermore move inside the main chamber from the hermetically sealed position, so as to cause the pressure inside the chamber to increase. The samples can be introduced into the main chamber through this venting port.

The secondary chambers can be closed on one side by means of caps through which cannulas belonging to the reagent management module can be introduced for injecting reagents or solutions, and on the other side with normally closed valves electrically, mechanically operated by the movement of the homogenization module rack, by means of an overpressure generated by the reagent management module.

In a particular embodiment of the invention, each homogenization container also includes a system of filters and a valve located in the sample outlet conduit. The filter is used to prevent solids having a size exceeding the desired size from accessing the reaction module. The valve isolates or communicates the homogenization container with the reaction module, allowing controlling the moment in which the processed sample must be injected in the reaction module.

In a particular embodiment of the invention the sample processing module is provided with a second subassembly consisting of the moving rack closing the homogenization chamber. During sample processing, this subassembly hermetically seals the top part of the homogenization chamber by means of a piston fixed to the rack and provided with a gasket. There is one moving rack for all the sample processing module containers, which are aligned with the rack by means of the sample processing module rotating drum. The rack is guided axially and operated by a stepper motor with screw-nut gear reduction. To that end, said rack is assembled on the sample distribution module shaft on one of the sides of said drum or moving device. This system allows very precise control of the axial advancement of the piston. In turn, the moving rack houses the reagent and solution management module cannulas and the sample homogenizer module piezoelectric system, which allows for precise positioning for injecting reagents, measuring parameters of the sample and performing homogenization. The advancement of the piston inside the homogenization chamber once the hermetical sealing is produced generates an overpressure in the solution or suspension to be treated, assuring the necessary contact between the piezoelectric system horn and the piston wall for generating cavitation in the solution or suspension.

In the described embodiment, the rack on which the piston is assembled for closing the container is located above the rotating drum with a vertical axis, but in the case that the rotating drum has a horizontal axis, said rack would be located on one side of the rotating drum such that the different containers may be located on the other side thereof. In any case, each one of the sample processing module containers can be provided with means for closing them. These means may consist of a piston or valve assembled in each container and operated by the movement of the homogenization module moving rack.

10.—Sample Reaction and Processing Controller

The sample reaction and processing controller is responsible for controlling the electromechanical mechanisms and sensors necessary for suitably processing the samples introduced in the sample processing module and injecting them in the reaction module after processing.

The reaction processing controller will be actuated by the overall control module, will carry out the preprogrammed functions and will send an electrical, analog or digital signal to the overall control module when its function has concluded, the same as when an error in its execution has been detected.

In the particular embodiment mentioned in section 9, the reaction processing controller is responsible for controlling the electromechanical components positioning the rack in the homogenization container, as well as the sensors used to learn the position of the rack and those which monitor the homogenization chamber.

11.—Reaction Module

"Reaction module" is defined as a device provided with a support on which there is a reaction chamber, communicated with the sample processing module by a main conduit and with the reagent and solution management module by another conduit. The reaction chamber houses a biosensor or sensor system capable of detecting substances (from molecules to entire microorganisms) present in the solution or suspension. Said sensor system can consist of at least one detecting substance in the form of a DNA or protein microarray (biochip), or any other system based on microfluidics. Said detecting substances can be chosen from the group formed by: a) a substance of an amino acid nature; b) a substance of a proteinaceous nature; c) a substance of a nucleotide nature; d) a nucleic acid; e) a peptide-nucleic acid (PNA); f) a substance of a lipid nature; g) a substance of a saccharide nature; h) a substance that is the combination of at least two of the previous ones; j) a live whole cell; j) a whole cell in the form of spore; k) a cell extract or lysate; l) a tissue formed by cells; m) a whole virus or any of its components; n) synthetic polymers and o) molecularly imprinted polymers (MIP). The proteins capable of binding specifically to other substances can be monoclonal or polyclonal antibodies. Furthermore, the sample modifying compounds can be chosen from a chemical reagent capable of binding to any one of the analytes present in the sample, or one or more substances from among those previously mentioned, or a combination thereof. Said microarray can be made up of a single type or a mixture of the mentioned detecting substances (for example a microarray containing DNA and protein points in a single carrier). The reaction chamber can function like a flow cell, such that the solution or suspension coming from the sample processing module circulates through said reaction chamber so as to allow the interaction of the substances present in the solution or suspension with the detecting substance or substances present in the sensor. The signal of the sample retained in the biosensor can be amplified by a cocktail or sample containing one or more substances of those mentioned above.

In a particular embodiment of the invention, the solution or suspension circulates from the sample processing module to the reaction module through a valve, a filter system and a main conduit. Once the sample is processed, it enters the reaction chamber through this main conduit. This same chamber has an outlet conduit connected with the waste storage container where the sample ends up once it has reacted with the detecting substance or substances present in the sensor. One or several additional conduits reach the reaction chamber directly from the secondary chambers of the sample homogenizer. These conduits allow injecting reagents, or simply the washing solution, into the reaction chamber before carrying out the reading or measurement of the reaction.

In a particular embodiment, once the solution or suspension is homogenized, it is made to react with a fluorescent reagent that may be incorporated (by means of a covalent, ionic, hydrophobic or other type of bond) to the substances (from molecules to whole microorganisms) present in said solution or suspension. Once said fluorescent reagent is incorporated, the excess thereof that has not reacted is inactivated by an inactivating substance preventing its subsequent reaction. Said inactivating substance may be a chemical blocking agent contributing an excess of functional groups reactive with the fluorescent reagent (for example amino, carboxyl, sulfhydryl or other groups). Once the inactivated fluorescent reagent excess is inactivated, the sample is filtered and injected into the reaction chamber continuously or discontinuously. Its passage through the reaction chamber allows interaction with the sensor detecting substances. Once the reaction occurs, the marked sample excess not retained in the sensor is eliminated by successive washings of the reaction chamber. The washing liquid is stored in the waste deposit.

In another particular embodiment of the invention, the signal of the retained sample in the sensor is amplified by a cocktail containing one or more substances (DNA, antibodies, PNA, etc) marked with a fluorescent substance, a metallic compound or an enzyme. Said cocktail is stored in one of the sample processing module secondary chambers until it is injected into the reaction chamber once the sample excess that has not reacted with the sensor has been washed. After a suitable incubation period, the excess of said cocktail not retained is eliminated with the washing solution.

The different reaction module chambers will be assembled in a moving device, for example in the distribution module moving drum.

12.—Reagent and Solution Management Module

"Reagent and solution management module" is defined as an assembly of devices for storing and precisely dispensing at the required time the different solutions and reagents involved in the different sample processing steps: homogenization, modification, reaction, washing, etc.

In a particular embodiment of the invention, the main element of the reagent and solution management module is made up of a motorized syringe carrying out the fluid storage and dispensing functions. The module is provided with the same number of identical assemblies of motorized syringes as different reagents necessary. Each assembly incorporates the following elements:

1. A syringe, fixed to the module rack, the capacity of which depends on the number of samples to be analyzed.
2. A linear actuator provided with a stepper motor actuating the syringe plunger rod. The actuator is designed in order to be able to precisely inject fluids in the corresponding chambers when these are at differential pressures defined by the functional process.
3. A position sensor determining the position of the syringe plunger, allowing open loop ("end of travel") or closed loop ("encoder") control of the assembly.
4. A passive (non-return) or active (motorized) valve maintaining the pressure barrier in the fluid circuits when the syringe is not actuated.
5. As a final element of the module, a cannula penetrates through the seals of the homogenization container side chambers. The cannula is fixed to the sample processing module moving rack and, therefore, its penetration movement is synchronized with the forward movement of said rack.
6. All the conduits and accessories necessary to connect the different components forming the fluid circuit.

In another particular embodiment of the invention, characterized by a significant number of reagents and/or solutions, the reagent and solution management module is formed by:

Several deposits, the same number as reagents and/or solutions that are to be used.

A single pumping system capable of aspirating the fluids of the different deposits and dispensing them to the homogenization or reaction chamber.

One or several distribution valves, each one of them provided with several inlet paths and one outlet path, capable of opening or closing the different conduits from the deposits to the homogenization or reaction chamber.

This configuration of the reagent and solution management module maximally simplifies the number of actuators required and the number of injection paths.

In another particular embodiment of the invention, characterized by a significant number of reagents and/or solutions, the reagent and solution management module is formed by:

- Several leak-tight syringe-deposits, the same number as reagents and/or solutions that are to be used, provided with a plunger without a rod, dividing the syringe-deposit into two sealed compartments: one provided with an outlet path with a non-return valve for the reagent or solution, and another one provided with an inlet path for the propulsion fluid.
- A closed propulsion fluid circuit formed by a single pumping system capable of aspirating said fluid from a deposit and dispensing it to the different sealed compartments of the syringes-deposit, thus actuating the plungers thereof.
- One or several distribution valves in the propulsion fluid circuit, each one of them provided with several outlet paths and one inlet path which allow selecting the syringe-deposit to be actuated.
- Individual outlet and injection paths for each syringe-deposit provided with a non-return valve and cannula.
- As an alternative to the previous point, a common injection path provided with a non-return valve and cannula connected with the outlet path of each syringe-deposit through one or several distribution valves.

This configuration of the reagent and solution management module maximally simplifies the required number of actuators and allows the injection of reagents/solutions through the individual paths, or optionally through a single path if fluid compatibility so allows this.

13.—Reagent and Solution Management Controller

The reagent and solution management controller is responsible for controlling the electromechanical mechanisms and sensors necessary to store and precisely dispense, at the required time, the different solutions and reagents involved in the different sample processing steps.

The reagent and solution management module controller will be activated by the overall control module, will carry out the preprogrammed functions and will send an electrical, analog or digital signal to the overall control module when its function has concluded, the same as when an error in its execution has been detected.

In the first particular embodiment indicated in section 12, the reagent and solution management module controller is responsible for controlling the actuator moving the syringe; for controlling the sensor determining the position of the plunger and for acting on the electrovalve maintaining the pressure barrier (see point 4 of the embodiment indicated in section 12).

14.—Data Reading Module

"Data reading module" is defined as the assembly of devices which allow detecting the reactions occurring in the reaction chamber and appropriately processing the detected signals.

In a particular embodiment of the invention, the reaction detector is a high resolution and sensitivity CCD reader with the optics and filters necessary to read only the electromagnetic radiation frequency produced as a result of the reaction. Said electromagnetic radiation is produced by energizing a reactive substance involved in the reaction process (fluorescent molecule). The energizing of said reactive substance is achieved with a monochromatic light beam from a laser diode. The CCD reader is opposite to the reaction chamber and the laser light beam strikes the reaction chamber with a certain angle to prevent reflections from striking the CCD reader.

The monochromatic light can be guided by means of a waveguide in which there is the biosensor which is energized as a result of the evanescent modes formed on the outer surface of the waveguide.

15.—Data Reading Controller

The data reading controller is responsible for controlling the devices used to detect the reactions occurring in the reaction chamber.

The data reading control module will be activated by the overall control module, will carry out the preprogrammed functions and will send an electrical, analog or digital signal to the overall control module when its function has concluded, the same as when an error in its execution has been detected.

In the particular embodiment indicated in section 14, the data reader control module is responsible for activating the laser during the pre-established time as well as for reading the information received from the chamber and suitably processing it (filtering, identification of the activated areas, quantification of the activated areas, etc.) and subsequently transmitting it to the overall control module.

The features and advantages of the apparatus and method of the invention will be better understood with the following description made in reference to the attached drawings in which a non-limiting embodiment is shown.

Figure 15:
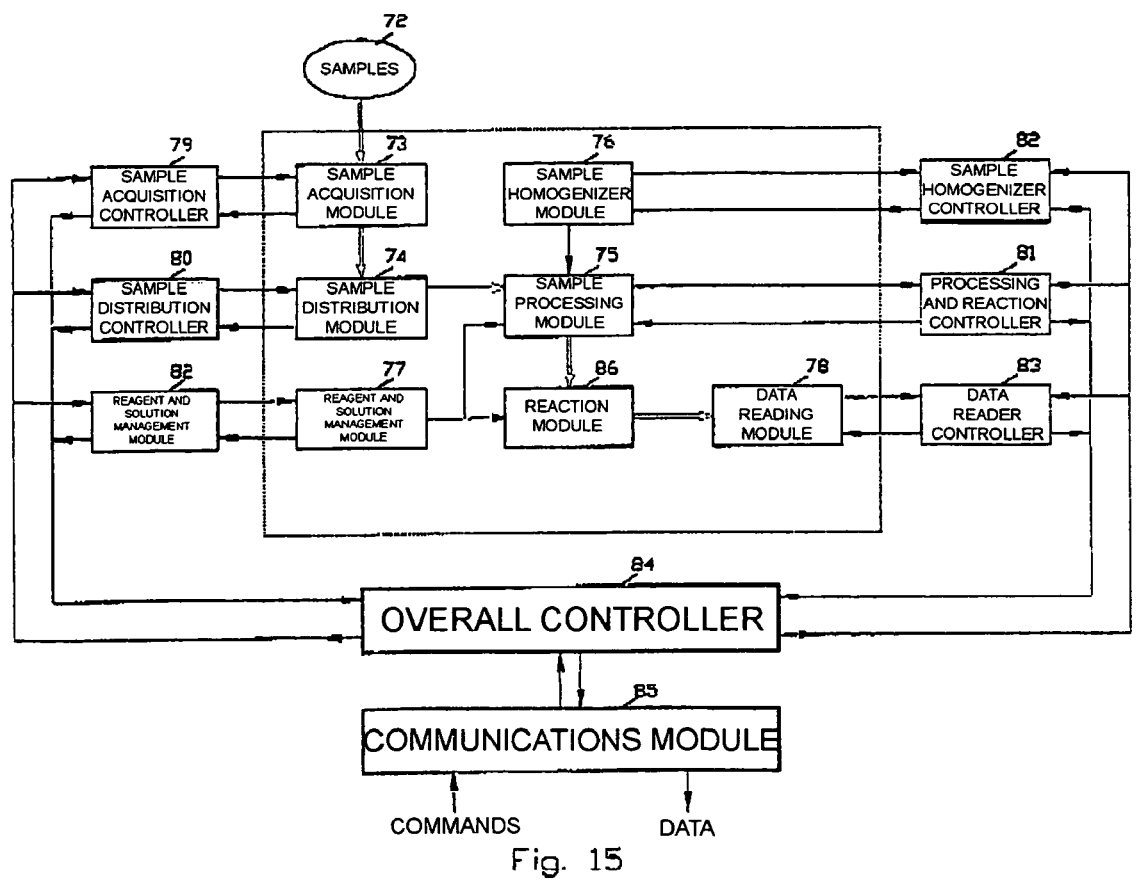

FIG. 15 corresponds to the working diagram of the apparatus of the invention.

Figure 16:
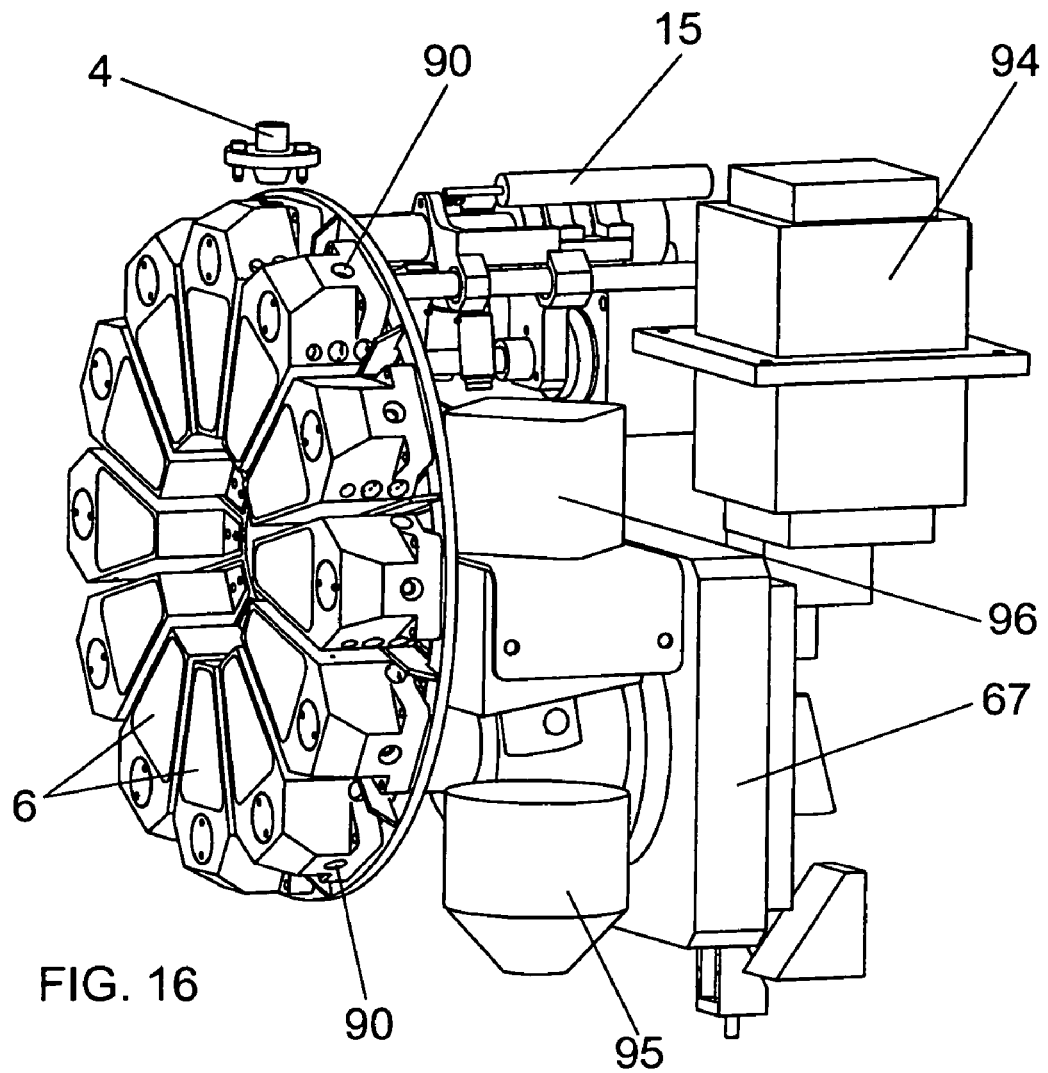
Figure 17:
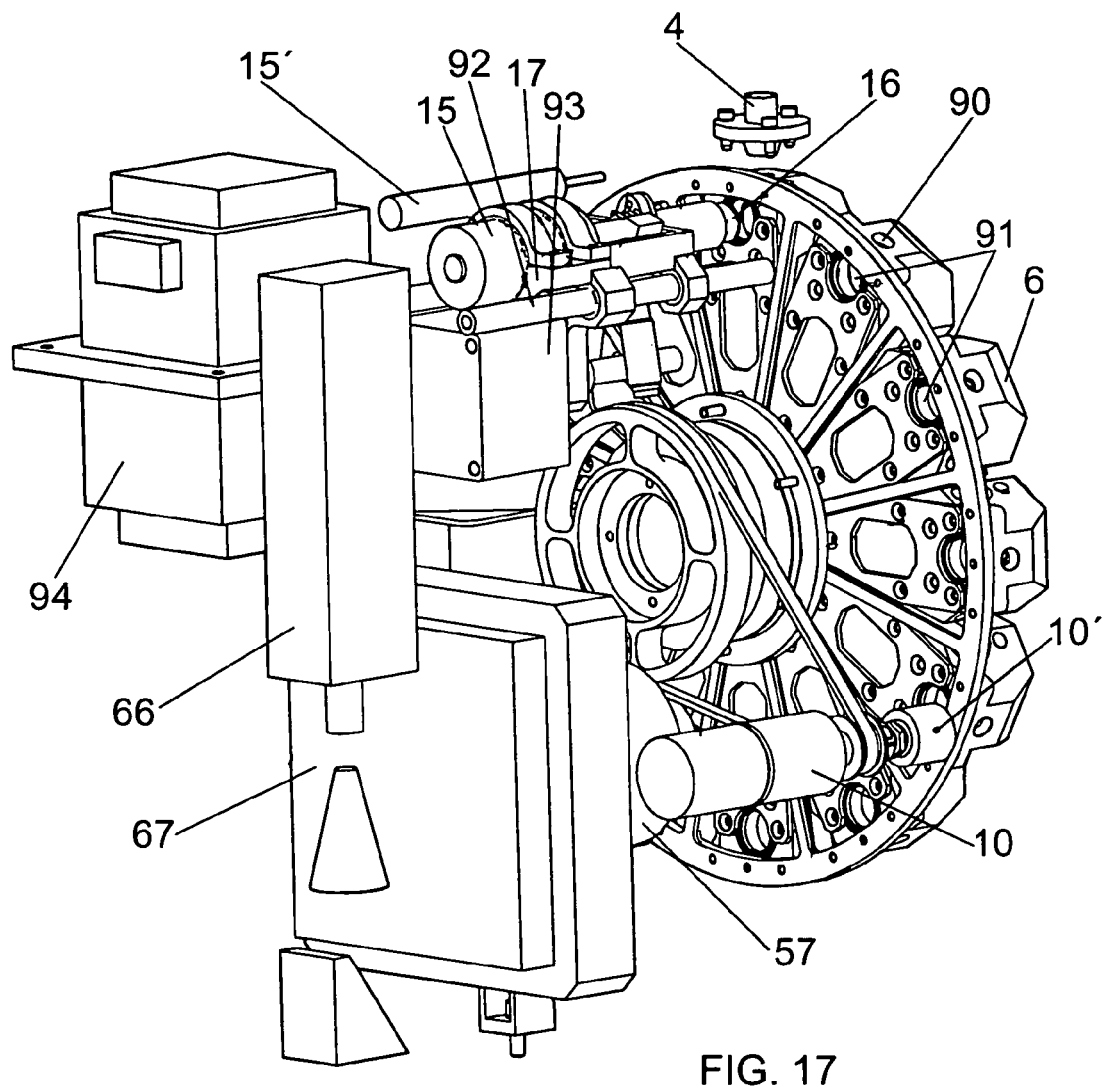

FIGS. 16 and 17 show front and rear perspective views of an embodiment variant of the apparatus of the invention.

The apparatus shown in the drawings consists of a robotized equipment allowing the detection of biomarkers (organic molecules and macromolecules of a biological origin) existing in the soil or subsoil. The method of detecting and characterizing such biomarkers is based on their interaction with an array of specific antibodies immobilized in specific positions of a solid support (called a chip or microarray).

This apparatus includes all the mechanisms, detectors and electronics necessary for automatically carrying out the experiment. The components used are primarily commercial, designed and/or selected to function under environmental conditions.

The different modules making up the apparatus of the invention will be described below for the purpose of facilitating the identification of the different components and the working thereof.

In the example depicted in FIGS. 1 to 14, the apparatus lacks the sample acquisition module, the samples to be analyzed being manually introduced. This is why the apparatus also lacks the corresponding acquisition module controller.

The apparatus comprises a rack made up of a top cover 1, a bottom cover 2 and a series of intermediate frames 3. This rack functions as a framework for the assembly of the different modules.

The sample distribution module includes a cylindrical hopper 4 (see FIG. 4), fixed to the top cover 1 of the rack and provided with a cone-shaped opening through which each soil sample of an approximate mass of 250 mg and a particle grain size of <0.5 mm is introduced. The bottom end of the hopper is provided with an inner cone 4', the function of which is to distribute the sample on the bottom of the container, belonging to the sample processing module, as will be explained below. The hopper 4 could be substituted with a fixed or moving adapter. The sample distribution module could furthermore be manually fed by an operator or by injectors of samples stored in multiwell plates.

The sample distribution module supports, houses and orients the components of the sample processing and reaction modules and is mainly formed by a rotating drum made of anodized aluminum, made up of two flanges: the top flange 5 (see FIG. 4) houses twelve sample processing module containers 6; the bottom flange 7 has devices for fixing the reaction module elements. Both flanges are assembled on respective angular contact bearings 8, slightly preloaded by the attachment screws thereof. The bearings, assembled on the central shaft 9 of the rack, allow the rotation of the drum about said shaft.

The rotation of the drum is carried out by a stepper motor 10, screwed to the bottom cover 2 of the rack, through a gear transmission made up of a pinion 11 fixed to the motor shaft, and a wheel 12 screwed to the bottom flange 7 of the drum. The motor has a resolution of 1.8°/step and is capable of providing a torque of 0.16 Nm. The gear transmission ratio is i=5:1, Then the final resolution of the rotating drum is 0.36°/step, which allows a resolution of 0.45 mm/step in the circumferential displacement of the axis of the sample processing module containers.

The initial position of the rotating drum is determined by an optical sensor 13 fixed to the frame 3 of the rack when the indicator 14 attached to the drum interferes with the sensor laser beam.

The sample homogenizer module includes an ultrasonic piezoelectric device formed by a commercial converter 15 (see FIG. 4) and a horn 16 firmly screwed to the end of the converter.

The converter 15 has a cylindrical shape (Ø 32 mm, length=89 mm) and is energized at a frequency of 40 kHz.

The horn (Ø 16 mm, length=49 mm), made of titanium (Ti 6Al 4V), is formed by cylindrical sections joined by smooth transitions. The free end of the horn ends in a planar circular flange (Ø 12.2 mm), which is in contact with the wall closing the sample processing module homogenization chamber.

This assembly is housed inside the longitudinally moving rack 17 closing the sample processing module main chamber, firmly fixed to it by means of a clamp 17' holding the cylindrical casing of the converter 15.

The converter transforms the high frequency electrical power supplied by the sample homogenizer control module into longitudinal vibrations which are amplified by the free end of the horn. The vibrations of the horn in turn generate pressure waves in the processed sample solution which cause cavitation in the solution, homogenizing the sample. The intensity of the cavitation, and therefore the degree of homogenization of the mixture, can be regulated by choosing the amplitude of the vibrations, being able to cover a range from gentle homogenization for low amplitudes to the breaking of cells for high amplitude levels.

The sample homogenizer control module controls the converter such that it tends to maintain the preselected amplitude by increasing or decreasing the supplied power according to the resistance found at the end of the horn. The device is designed to supply a maximum output power of 130 w.

The sample processing module is provided with two clearly differentiated subassemblies (see FIGS. 4 to 6):
the homogenization container 6 and the moving rack 17 closing the homogenization chamber.
the homogenization container 6 contains the sample deposited in it by the sample distribution module during the homogenization process.

The apparatus is designed to house up to twelve homogenization containers, allowing for the analysis of a single sample per container.

The containers are made of transparent acrylic plastic in order to be able to view the homogenization process.

Each container is provided with a main homogenization chamber 18 surrounded by four secondary chambers 19, 20, 21 and 22 connected to it by conduits 23 of different sizes.

The cylindrically shaped homogenization chamber 18 (Ø 19 mm, length 22 mm) is open at its top part in order to receive the samples in the solid or liquid state provided through the hopper 4. During sample processing, this opening is hermetically sealed by the piston 24 of the moving rack 17. The bottom of the chamber is provided with a port 25 of Ø 10 mm through which the homogenized mixture is injected into the reaction module. The cylindrical wall of the chamber is provided with a venting port of Ø 0.5 mm, not shown, located at a height of 9.3 mm above the bottom of the chamber, which determines the moment of the hermetic sealing of the chamber when the gasket 26 carried by the piston of the rack seals said port.

The secondary chambers 19 to 22 are hermetically sealed with silicon caps 27, both in their upper and bottom parts, and communicated with the main chamber by means of a conduit 23. The container has the following secondary chambers:

The fluorescent marker chamber 22: this is a cylindrical chamber (size=Ø 4×7 mm) joined to the main chamber trough a conduit 23 of Ø 1 mm. It internally houses 1 mg of a fluorescent marker compound, in the solid state, adhered to the bottom of the chamber. This chamber is used to inject the saline solution through the reagent and solution management module cannula 28 necessary for preparing 1 ml of sample solution. During the injection of the saline solution, the fluorescent marker is dissolved and introduced into the homogenization chamber 18, forming part of the sample solution.

Blocking agent chamber 21: this is a cylindrical chamber (size=Ø 4×4 mm), joined to the main chamber through a conduit 23 of Ø1 mm. This chamber is used to inject the BSA blocker solution through the reagent and solution management module cannula 29 necessary for blocking the fluorescent marker excess which has not reacted with the molecules of the sample. Located under the bottom cap 27 of this chamber there is a cone-shaped port in which the Luer coupling 28' of the reaction module washing conduit is housed.

Pressure sensor chamber 20: this is a cylindrical chamber (size=Ø 4×5 mm), joined to the main chamber through a wide conduit 23 of Ø 4 mm, for the purpose of facilitating the entrance of dissolution into it. During the homogenization process, this chamber houses the cannula 29', carried by the moving rack 17, which is connected with the pressure sensor 30 responsible for monitoring the differential pressure of the process.

Temperature sensor chamber 19: this is a chamber that is identical to the pressure sensor chamber. During the homogenization process, this chamber houses the cannula 31, carried by the moving rack 17 which in turn houses the temperature sensor probe 32, responsible for monitoring the sample solution temperature during said process.

The surfaces of the bottom of the sensor chambers 19 and 20 and the bottom of the homogenization chamber 18 are treated with a surfactant so as to facilitate the penetration of the solution into said secondary chambers.

Each homogenization container also includes a filter 33 of Ø12 mm and provided with a pore diameter of 20 µm used to prevent solids having a size exceeding the desired size from accessing the reaction module. The filter is located on the filter holder 34, which is housed inside the screw-on cap 35. This assembly is screwed onto the base of the container, under the homogenization chamber outlet port. A gasket 36 provides the necessary leak-tightness of the assembly.

The screw-on cap 35 is provided with a male Luer cone to which the non-return valve 37 is connected. This valve connects the homogenization container 18 with the reaction module. The valve is usually closed due to the overpressure of 1.3 bar existing in the reaction module, isolating both modules. A usually closed and electrically actuated valve, or one actuated mechanically by the movement of the homogenization module rack, could be arranged instead of the non-return valve 37.

Figure 1:
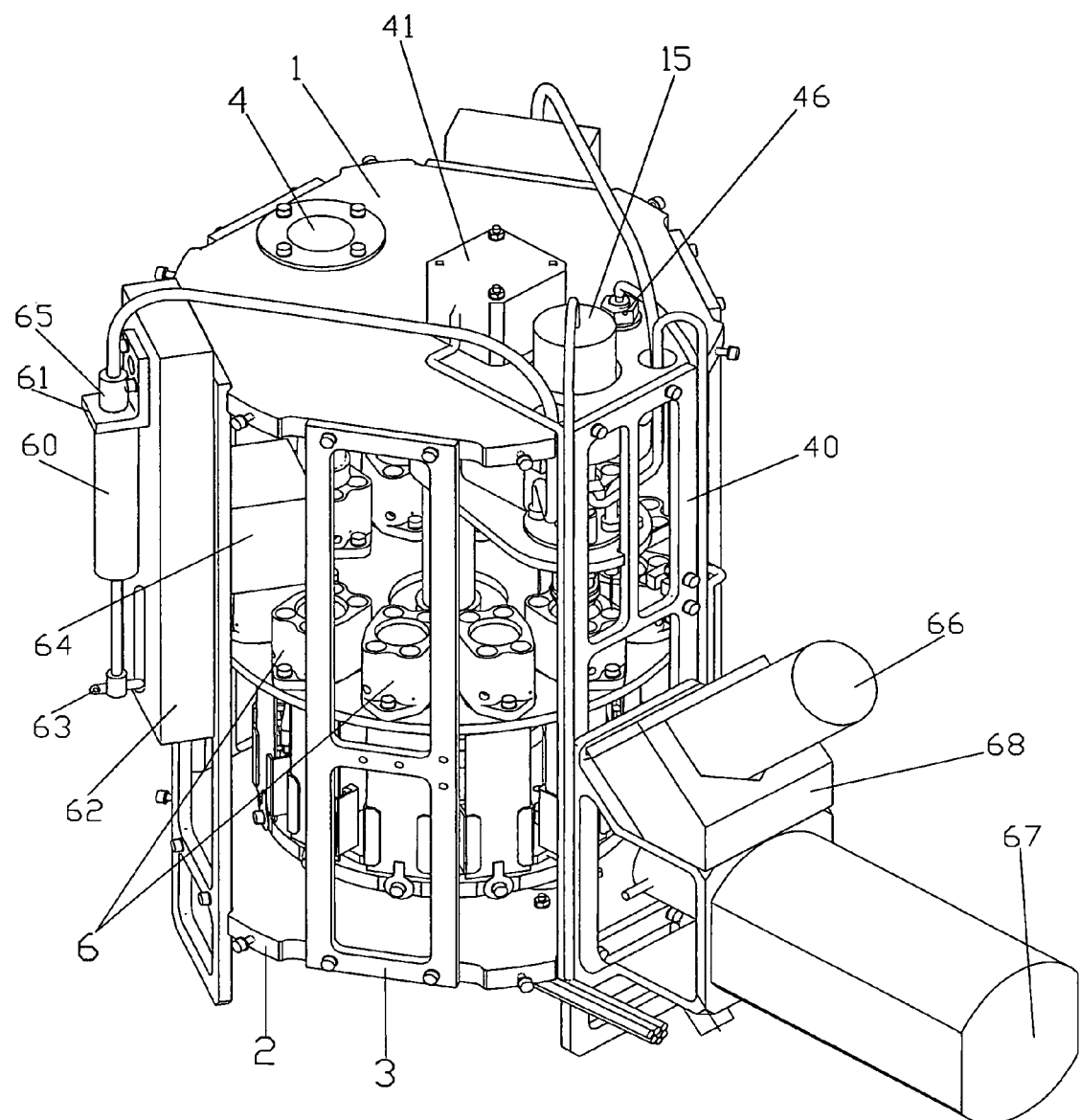
FIG. 1 shows a front isometric view of the apparatus of the invention.
Figure 2:
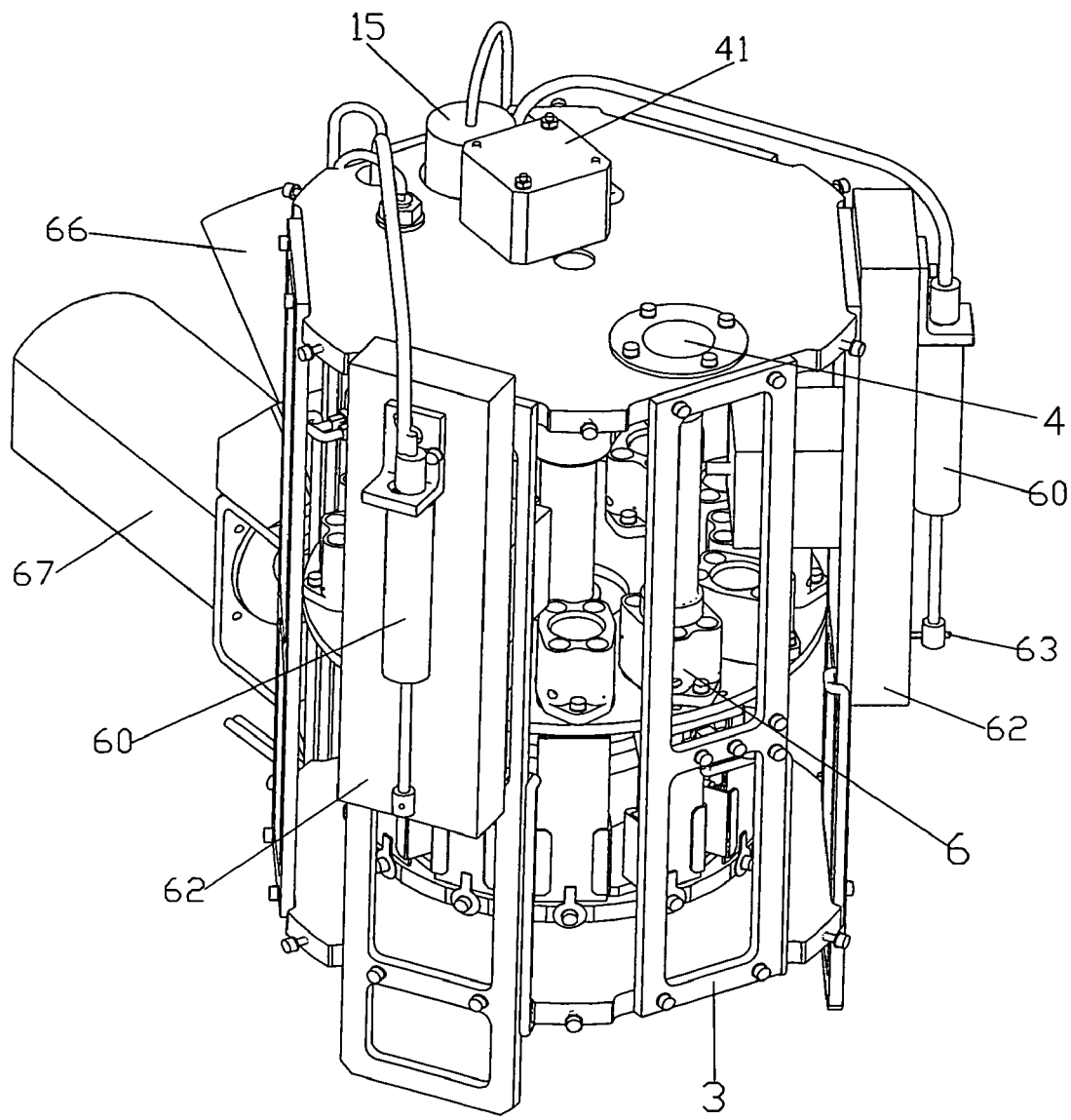
FIG. 2 shows a rear isometric view of the apparatus of the invention.
Figure 3:
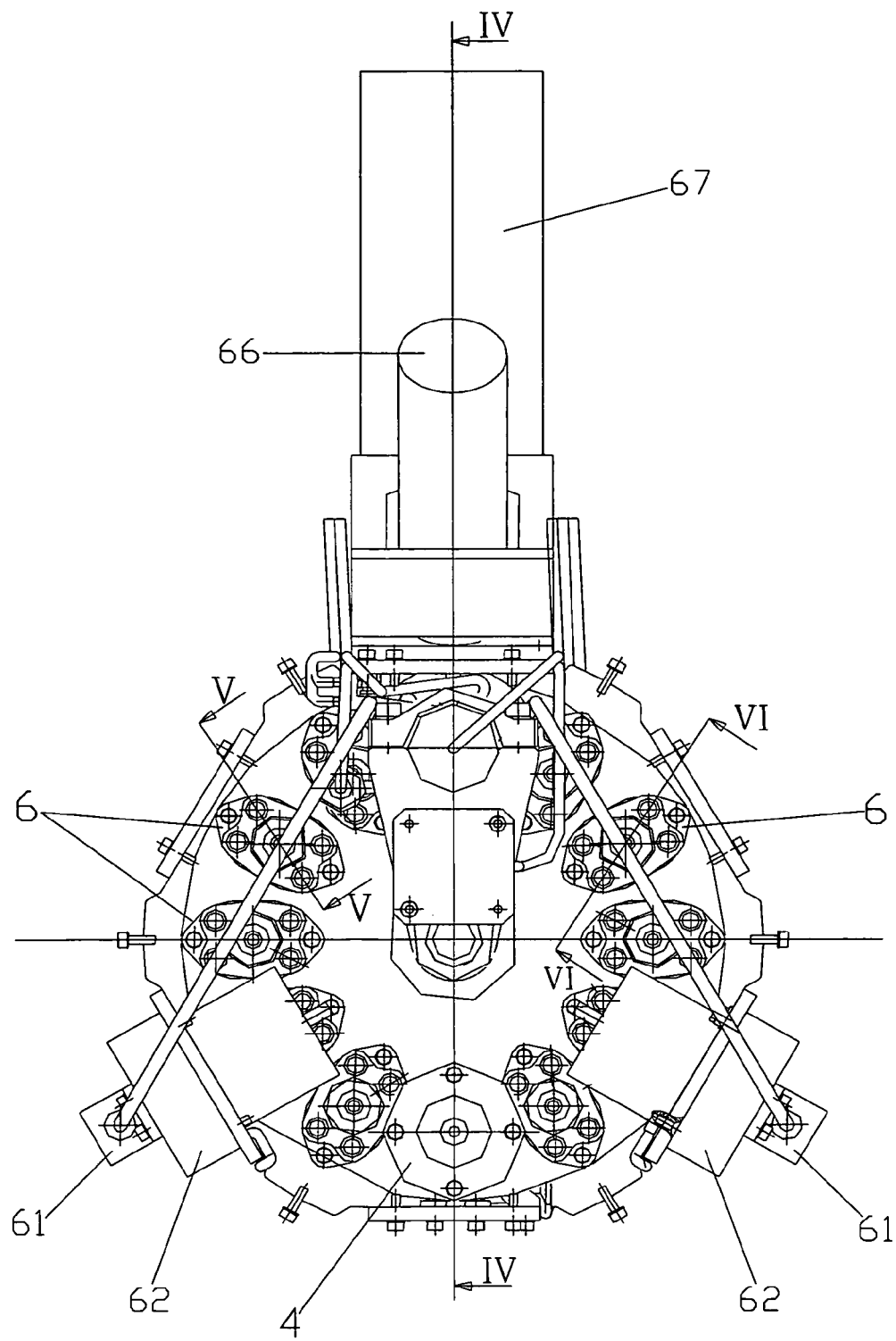
FIG. 3 shows a top view of the apparatus of the invention in which the top cover has been removed.
Figure 4:
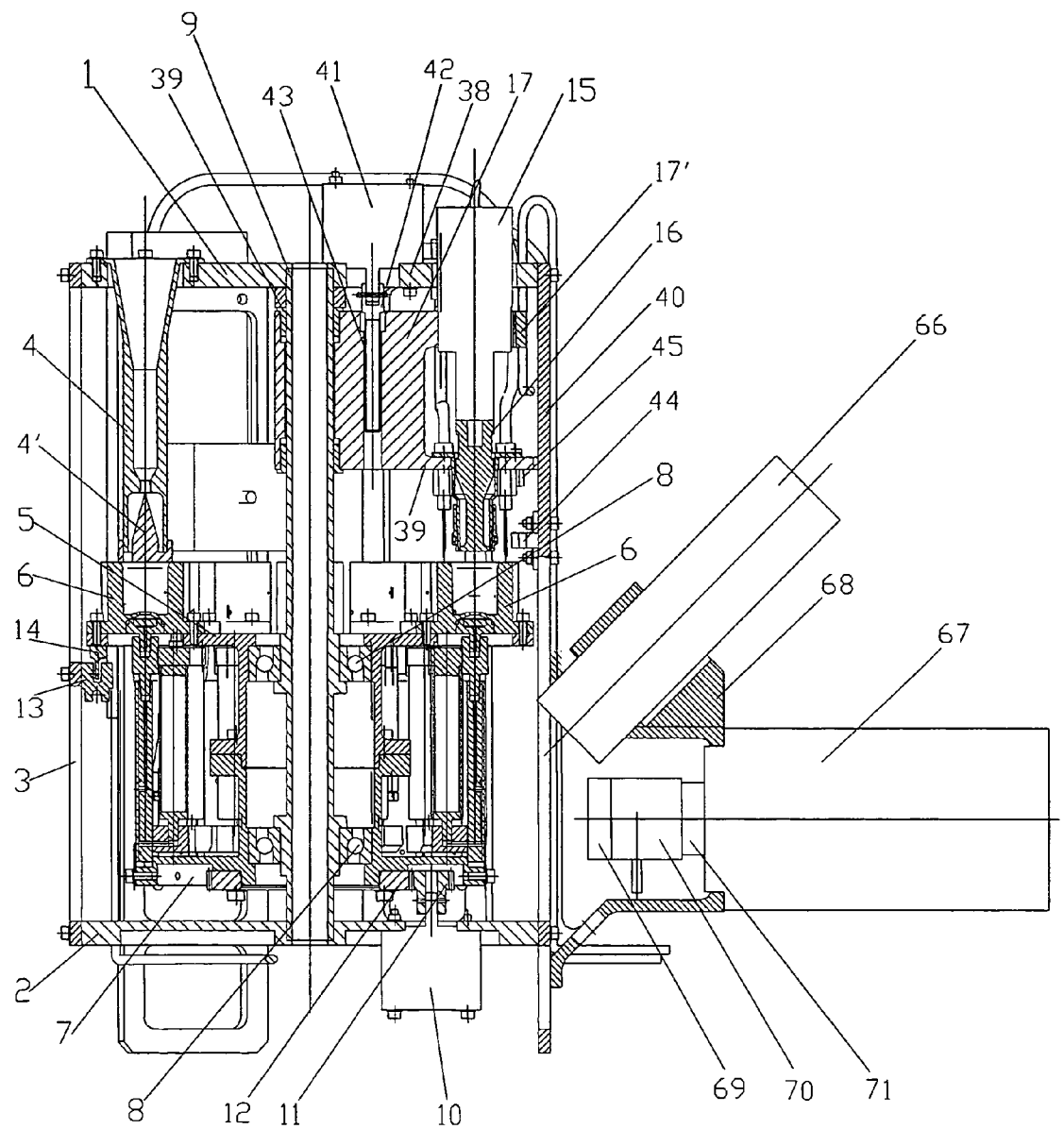
FIG. 4 shows a section according to the IV-IV section line of FIG. 3.

The moving rack 17 closing the homogenization chamber, FIG. 4, carries out the hermetic sealing of the top part of the homogenization chamber 18 during sample processing.

There is one moving rack for all the module containers which are aligned with the rack by means of the sample distribution module rotating drum.

The subassembly consists of the rack 17, made of aluminum, which houses the different subassembly elements. It is provided with a top flange 38 for fixing the converter 15 of the sample homogenizer module. A bottom flange 39 in turn houses the piston 24, the reagent and solution management module cannulas 28 and 29, and the pressure and temperature sensor cannulas 29 and 31, respectively.

The rack slides along the shaft 9 by means of two bushings 39 and is axially guided along the central rib of the frame 40.

The axial movement of the rack is carried out by a stepper motor 41 screwed to the top cover 1 of the rack, through the transmission of the screw 42 fixed to the motor shaft and the nut 43 housed in the body of the moving rack 17. The motor has a resolution of 1.8°/step and is capable of providing a torque of 0.16 Nm. The screw is provided with an M6×1 thread, then the final resolution of the rack movement is 5 µm/step, allowing for very precise control of said movement which in turn translates into precise positioning for the injection of reagents, sample parameter measurements and performance of ultrasonic homogenization.

The final moving rack position is determined by an optical sensor 44 fixed to the frame 40 of the rack when the indicator 45 joined to the bottom flange of the rack interferes with the sensor light beam.

Figure 5:
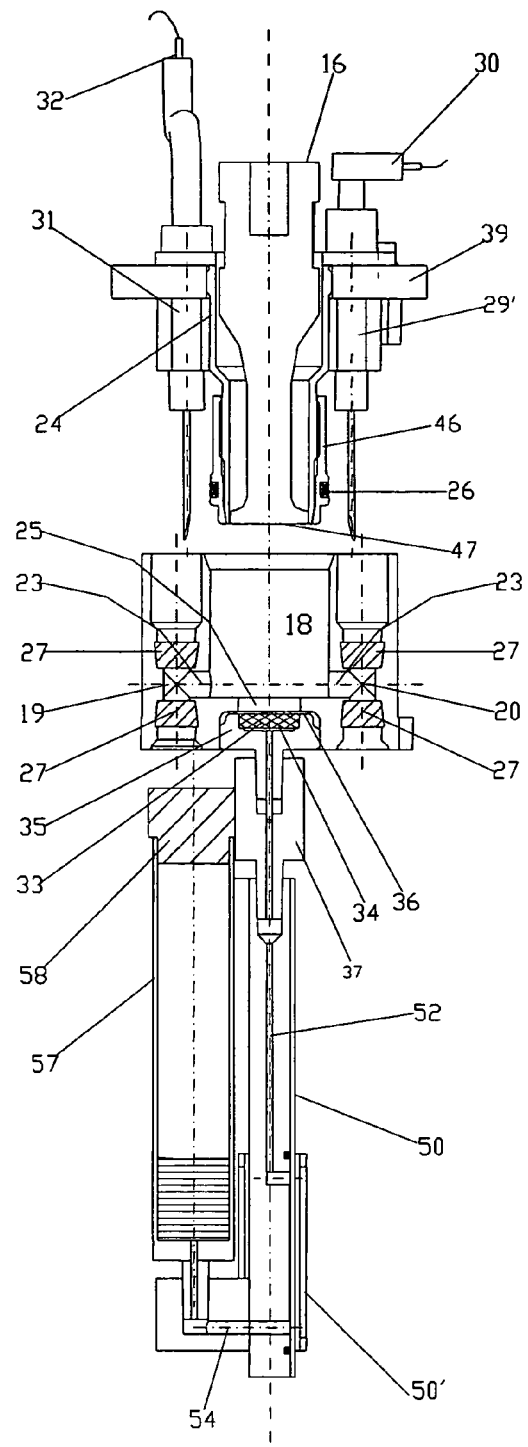
FIGS. 5 and 6 show vertical sections of the processing module and reaction module according to the V-V and VI-VI section lines of FIG. 3, respectively.
Figure 6:
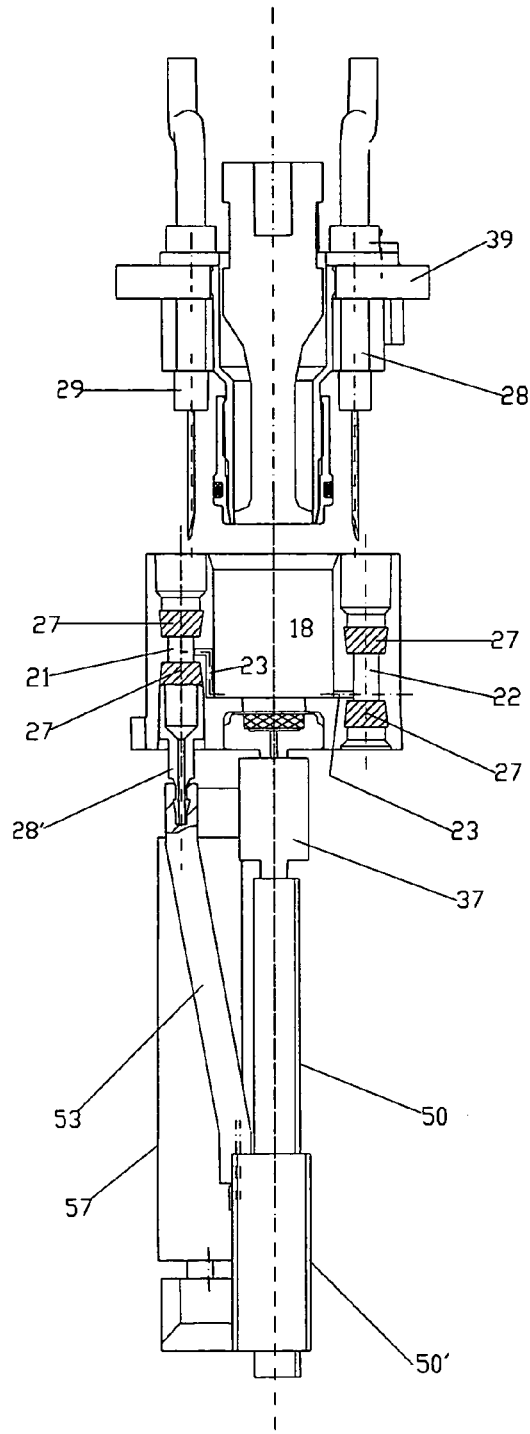
Figure 7:
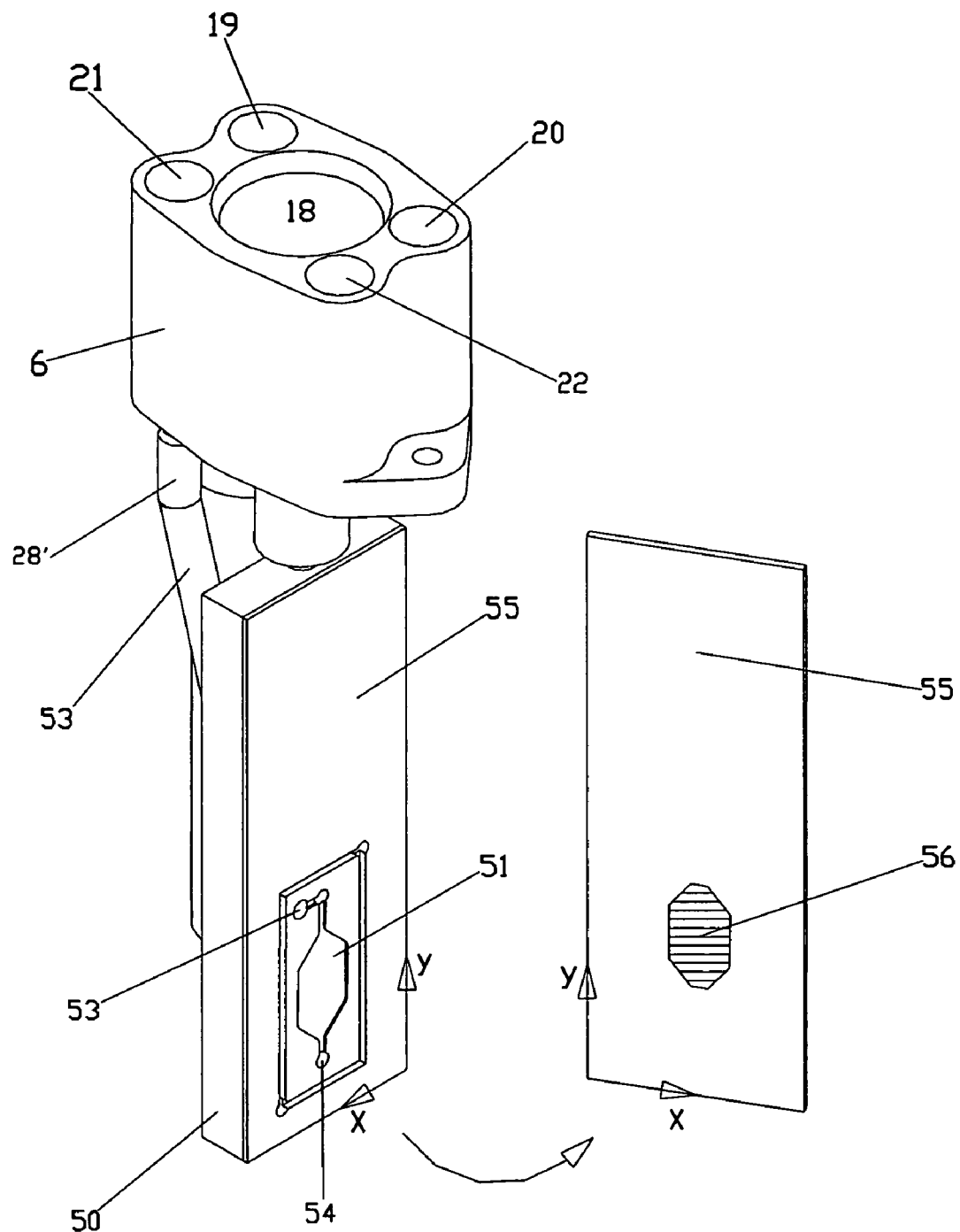
FIG. 7 shows an isometric view of the reaction module.
Figure 8A:
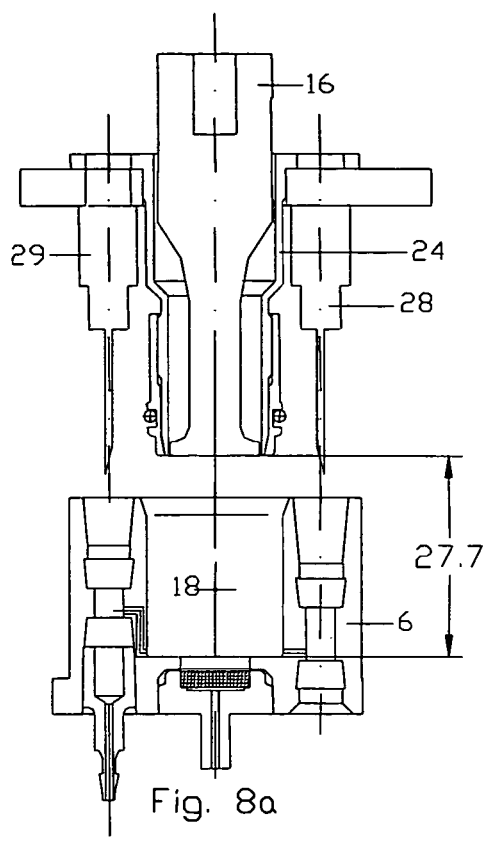
FIGS. 8 to 14 show different positions of the sample processing and homogenization modules throughout the process.
Figure 8B:
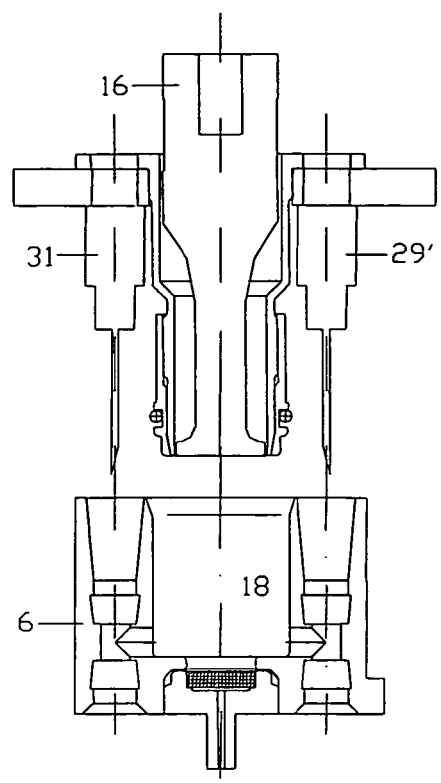
Figure 9A:
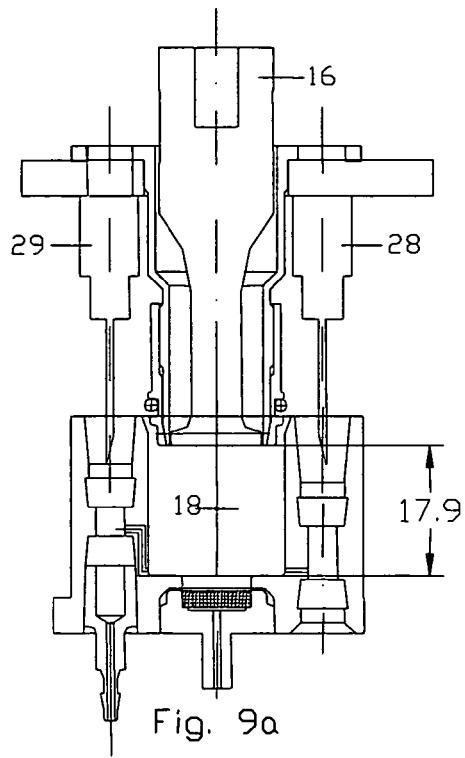
Figure 9B:
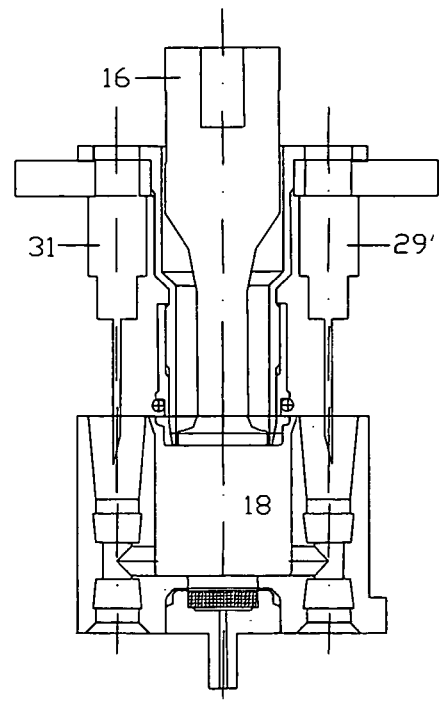
Figure 10A:
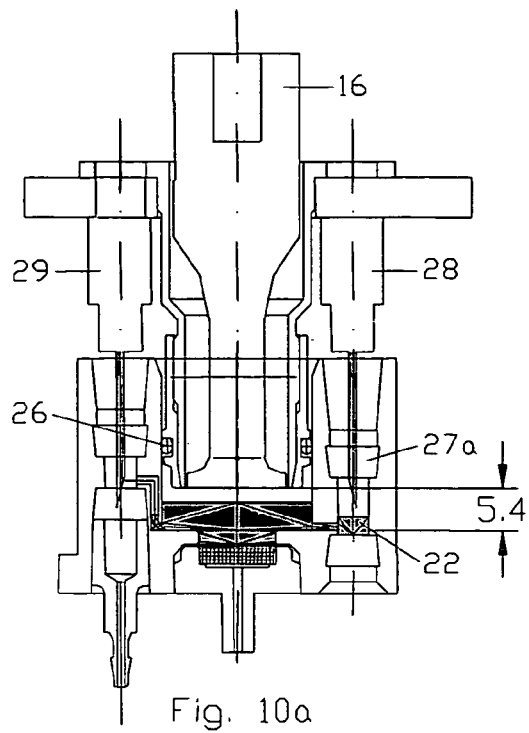
Figure 10B:
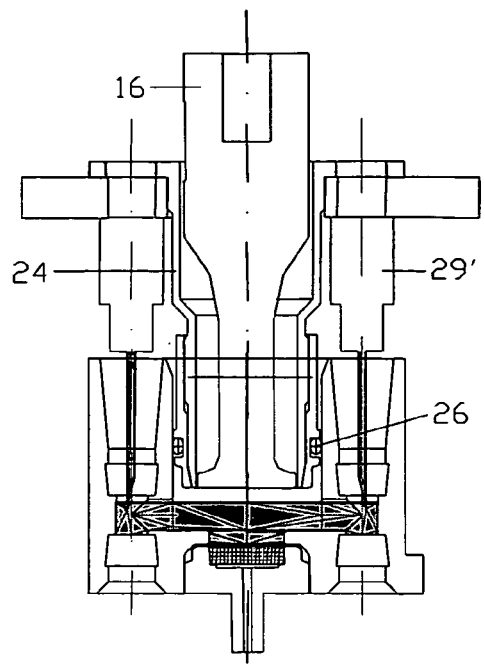

The piston 24, FIG. 5, made of stainless steel, is a hollow revolving part provided with a top flange with which it is fixed to the moving rack. The bottom end ends in a cone and has assembled thereto the threaded bushing 46 which is provided with a gasket 26. Both parts are screwed together, firmly holding the membrane 47 by means of the pressure exerted by the inner cone of the bushing 46. The membrane 47 is made of PTFE and has a thickness of 0.1 mm. The inside of the piston houses the sample homogenizer module horn 16, which rests on the membrane 47. This assembly hermetically seals the top opening of the homogenization chamber as a result of the leak-tightness produced by the gasket 26 and the membrane 47. The forward movement of the piston 24 inside the homogenization chamber once the hermetic seal thereof has been produced generates an overpressure in the solution to be treated, assuring the necessary contact between the piezoelectric system horn 16 and the membrane 47 of the piston for generating cavitation in the solution.

The pressure sensor 30 monitors the overpressure of the homogenization chamber. It is based on a Wheatstone bridge and its main features are:
Measurement range: 0÷207 kPa
Energizing voltage: 10 V
Output signal full-scale: 100 mV
Output signal sensitivity: 0.483 mV/kPa The overpressure parameter in the chamber is used to control and define the homogenization position of the piston-homogenizer assembly. The reaction and processing controller inhibits the motor 41 of the moving rack when the overpressure in the chamber reaches the value of 0.8 bar. It is also used to control and define the homogenization time. The sample homogenizer control module inhibits the piezoelectric system converter 15 when the overpressure in the chamber exceeds the value of 1.0 bar.

The temperature sensor 32 monitors the temperature of the sample solution during the homogenization process. It is based on a probe provided with a K-type thermocouple housed in a stainless steel sheath of Ø0.5 mm and 250 mm in length. The probe is fixed on the top cover 1 of the apparatus by means of a threaded stud whereas its free end is introduced in the cannula 31, which facilitates the insertion of the probe through the silicon caps 27.

The sample solution temperature parameter is used to control and define the homogenization time. The sample homogenizer control module inhibits the piezoelectric system converter 15 when the solution temperature exceeds a predetermined critical value.

The reaction module (see FIGS. 5 to 7) consists of a parallelepiped support 50 (size: 76×26×6.5 mm), where there is an open cavity 51, called the reaction module, having a symmetrical irregular hexagonal shape (overall dimension: 14×8 mm), with a depth of 0.3 mm. This chamber is provided with the following access paths:
Homogenized solution or suspension inlet path 52. This is in the top corner of the chamber and is formed by a conduit of Ø1 mm, ending in a female Luer cone for the leak-tight connection with the sample processing module 75 non-return valve 37.
Washing solution inlet path 53. Located in the top corner of the chamber and is formed by a conduit of Ø 2.5 mm for the leak-tight connection of the washing conduit 28'.
Solution outlet path 54. Located in the bottom corner of the chamber and is formed by a conduit of Ø 2 mm, ending in a female Luer cone for the leak-tight connection with the waste deposit 57.
The inlet ports 52 and 53 and the outlet port 54 can be connected by a conduit provided with a pumping system, not represented, which will allow the recirculation of the sample on the biosensor. The chamber 51 may further include a system for stirring or moving the liquid sample to improve the biosensor operation.

The reaction chamber 51 has a thin coating of the hydrophobic agent SIGMACOTE for the purpose of improving circulation of the different fluids, preventing the adhesion of solid particles and molecules to its surfaces.

The reaction chamber 51 and its access paths are closed by means of a glass slide 55 (size: 75×25×1 mm), on the inner side of which, coinciding with the chamber, the biosensor or sensor system 56 capable of detecting substances present in the homogenized solution, from molecules to whole microorganisms, is deposited. This sensor system is made up of different detecting substances in microarray form.

The slide 55 is fixed to the support 50 by means of two clips 50'. The leak-tightness of the attachment is assured by a rectangular CV-1152 silicon perimeter that is injected through two ports located on the opposite side of the support 50. Once the silicon is cured, it forms a sealing gasket having a 1×1 mm section surrounding the reaction module and its access paths.

The washing conduit 28' is formed by a plastic pipe with an inner diameter of 1.6 mm and an approximate length of 90 mm. It is provided at its open end with a metallic coupling, ending in a male Luer cone, which is hermetically connected in the housing of the homogenization container 18 under the blocking agent chamber. It has a bent plastic coupling at the bottom end for the leak-tight connection with the reaction module washing path.

The waste deposit 57 is formed by a plastic syringe with a 5 ml capacity provided with an eccentric male Luer cone connected to the reaction chamber outlet path. The syringe lacks a plunger and has instead a silicon cap 58 hermetically sealing its top opening.

The waste deposit 57 can be common for all the reaction modules and be connected to the outlet thereof by means of a cannula assembled on the sliding rack.

The assembly is made with transparent materials (glass, acrylics, etc.) in order to be able to view the fluid circuits.

Once chamber 18 is assembled and connected to the sample processing module homogenization container 6, together with its access paths, conduits and deposit form a leak-tight circuit which has previously been filled with saline solution at an overpressure of 1.3 bar. The solution level in the waste deposit 57 is 1 ml, the rest of the deposit being filled with air pressurized at said overpressure.

The apparatus is designed to house up to twelve reaction modules, allowing the analysis of a single sample per module.

The reagent and solution management module consists of all the elements necessary to store and precisely dispense, at the required time, the different solutions and reagents involved in the different sample processing steps.

The reagent and solution management module main element (see FIGS. 1 and 2) are made up of a motorized syringe 60 carrying out the functions of fluid storage and dispensing. The module consists of two identical assemblies of motorized syringes: one intended for the saline solution used to dissolve the solid sample and the other one intended for the BSA blocker solution which in turn carries out the reaction chamber washing solution functions. In the case that the fluids were in the reagent management module, the apparatus could include a device that injects them into the reaction chamber.

Each assembly incorporates the following elements:

1. A commercial motorized syringe 60 (size: 203×56×94 mm) fixed to a frame 3 of the structure of the apparatus through a base plate. Its main components are:

Syringe 60 with a 10 ml capacity provided with a male Luer cone with a locking closure. The end of the cone is fixed to the support 61 which in turn is screwed to the base plate 62 of the assembly. The plunger rod is screwed to the linear actuator rod 63.

A linear actuator provided with a stepper motor 64 actuating the syringe plunger rod. The actuator is designed to exert a maximum force of 89 N. The resolution that is obtained when injecting with no overpressure is 10 μl/step.

An optical sensor, not shown, housed on the base plate, determining the position of the syringe plunger, allowing open loop control of the assembly.

2. A non-return valve 65 maintaining the pressure barrier in the fluid circuits when the syringe is not actuated.

3. A threaded cannula (size: Ø 1×20 mm), not shown, which as a final element of the assembly penetrates through the silicon caps of the side chambers of the homogenization container 18. The cannula is fixed to the sample processing module moving rack 17 and therefore its penetration movement is synchronized with the forward movement of said rack.

4. All the conduits and accessories (size: ⅟₁₆") necessary to connect the different components forming the fluid circuit.

A data reading module includes the components allowing detecting the reactions occurring in the reaction chamber.

It is mainly made up of a laser diode 66 (see FIGS. 1 and 4) and a CCD camera 67, both being commercial and assembled on a bracket 68 screwed to the frame 40 of the structure of the apparatus.

The laser diode 66 emits a monochromatic light beam with a 635 nm wavelength and a sufficient width to irradiate the entire reaction chamber 51, energizing the fluorescent molecules. It is assembled on the bracket 68 such that the light beam strikes the reaction chamber plane at 45°, preventing the reflections from occurring in the direction of the CCD camera axis. The laser diode 66 housed in a cylindrical casing (size: Ø 38×158 mm), has a maximum power of 250 mW and has a cooling system which allows regulating the diode temperature.

The CCD camera 67 detects the electromagnetic radiation emitted by the fluorescent molecules when they are energized by the laser light beam. Said radiation, with a spectral band centered at 670 nm, corresponding to the maximum emittance of the fluorescent dye Cy5 used as a marker. For the purpose of preventing the entrance of radiations of other wavelengths in the CCD, the camera is provided with a 695AF55, emission filter 69 with a 25 mm diameter. A lens 70 and a separator 71 which allow focusing and amplifying the image in the CCD complete the device. The three components, filter, lens and separator, are commercial products.

The camera is a digital, black and white, high resolution and high sensitivity camera. It has the following features:

Size: 146×76×64 mm
Sensor: CCD with 1280×1024 pixels
Square pixel size: 6.7×6.7
Sensor size: ⅔"
Dynamic range: 12 bits
Sensitivity: 4350 e/lux/um2/s
Refrigerated As can be understood, depending on the needs, the capacity of the apparatus could be adapted, including if necessary two or more sample homogenizer and sample processing modules, as well as two or more sample distribution modules.

As indicated, the apparatus includes a communications module (communications module) which is the interface of the equipment with the user, the equipment being able to be locally or remotely operated through the suitable communications protocols.

The communications module corresponds to software developed in LabView®, of National Instruments®, which is run in the device control system and implements the protocol machine necessary to establish the communications links, regardless of the connection through which it is controlled. This connection can be any of the following:

Console in the case of a local user.
Link via RS232, RS422 or RS485 series.
Parallel link.
USB (Universal Serial Bus) link.

TCP, UDP, or IP link, or any other protocol for data transmission between computers.

Radio, IRDA links . . .

Field buses: PROFIBUS, CAN, FieldBus, InterBUS-S, . . .

Telephone links: GSM,

In the case of the data link establishment, the communications module carries out data coding, encapsulation, control of access to the medium, sending/receiving data/commands and implementing safety options by means of the validation of all the commands.

There is an overall controller and one controller per module for control of the assembly.

The overall controller (overall control module) implies the overall system supervisor of the process and each one of the modules making up the invention. It may further allow for the local and remote operation of the apparatus.

Considering the control system as a PC architecture with input/output cards running software developed in Lab View®, from National Instruments®, the overall control module corresponds to the main process interacting with the remaining controllers to carry out the overall process and analysis. It carries out the following functions:

Receiving the messages form the communications module; validating the parameters and commands received; interpreting such commands (tasks) sent by the user.

Task execution system: overall sub-process sequencing, sending commands to the corresponding local controllers.

Carrying out preprogrammed automatic tasks.

Supervising the working of each module: carrying out subtasks and safety verifications (monitoring the process parameters and checking their inclusion in the corresponding suitable working ranges). Emergency stop control if safety so requires this.

Recovery from subsystem failures.

Sending the working parameter values to the operator for their general process monitoring through the communications module.

Receiving, preprocessing and sending the data received by the data reading module to the computer.

The sample distribution module controller is a process which is run in the control system in addition to several cards for control of the stepper motors, as well as other digital inputs and outputs for reading the sensors.

It is responsible for executing the subtask involving the distribution of the samples collected by the sample acquisition module among the different sample processing modules.

The sample distribution control module must be able to carry out the following tasks:

Knowing at all times the position of each sample processing module.

Suitably positioning the sample processing module.

Carrying out a local supervision with respect to the sample distribution module.

Receiving commands from the overall controller.

Sending data corresponding to the current status to the overall controller.

The sample distribution control module has the information from the ends of travel and linear or angular position encoders, as well as control over the actuators making up the sample distribution module. With the suitable instructions from the overall controller, the sample distribution control module will operate on the actuators so as to situate the suitable sample processing module under the sample acquisition module.

Considering a sample distribution module made up of the rotating drum described above, to which a stepper motor for the movement and end of travel optical sensor is joined, the task of the sample distribution control module consists of observing the commands from the overall controller by making the drum rotate to the desired position.

A first overall working phase involves a calibration of the sample distribution module as a result of which the distribution module controller takes the drum to the position in which the end of travel optical sensor is activated, which involves a known position. The distribution module controller will thus know thereinafter the absolute position of the drum.

By means of the corresponding command from the overall control module, the distribution module controller can take the sample processing module to any desired position through the suitable number of steps of the motors, which information is handled by this controller.

The reagent and solution management control module controls those devices intended for providing the solutions necessary to carry out the entire biochemical process.

As with the previous controllers, the reagent and solution management control module consists of a subprocess running in the control computer together with the cards for the control of the stepper motors, and of digital inputs for the reading of the sensors.

The reagent and solution management control module allows:

Supervising the status and the operation of each one of the devices making up the reagent and solution management module: capacity, availability, errors/failures occurring in the devices, Actuating such dispensing elements for the injection of precise and specific amounts of the solutions into the reaction chambers.

Receiving commands from the overall controller and sending data thereto regarding status.

In the configuration of the previously described reagent and solution management module, the actuation of the stepper motors controlling the syringe allow the injection of a precise amount of solutions into the system.

The reaction and processing controller is responsible for controlling the electromechanical components which position the moving rack in the homogenization container, as well as the sensor which determines the position of the moving rack.

The reaction and processing controller is also responsible for monitoring and supervising the parameters (pressure and temperature) involved in the process.

The information from the different sensors monitoring the process must be analyzed at all times for the purpose of determining whether or not it is being carried out within the allowable ranges.

The result of this analysis is sent to the overall controller, which makes the appropriate decisions within the overall process.

In relation to the sample homogenization process monitoring, the reaction and processing controller consists of two sensors, a pressure sensor and a temperature sensor, as well as the hardware elements for the conditioning of these signals through which the physical parameters under which the reaction is carried out can be measured. The analysis of these parameters can determine the time during which a given subprocess is carried out if reaching an established temperature is considered as a criterion for concluding it.

The data reader control module is the means through which it is possible to interact with the data reading module. It must allow:

Actuating the mechanisms for the analysis of the results obtained after the reaction carried out in the reaction module provided by the data reading module. This actuation will be carried out after the corresponding command from the overall controller.

Acquiring the reaction results which are provided by the data reading module.

Supervising the data reading module status.

Processing the information obtained from the reaction.

Sending all the previous information to the overall controller through certain commands sent by said overall controller.

FIG. 15 corresponds to the working diagram of the described apparatus:

The samples 72 to be analyzed are taken by the acquisition module 72, which includes them in the distribution module 74, and from there they go to the processing module 75 where they are homogenized by the homogenization module 76. The samples finally go to the reaction module 86 which is communicated with the reagent management module 77, data finally being taken by the data reading module 78.

Each one of these modules is supervised by the corresponding controller 79 to 83, and the assembly by the overall controller 84, which is managed through the communications module 85.

The functional description of the apparatus of the invention is detailed in the following sections, taking two aspects into account: the substance detection process and the robotized operational sequence of said apparatus.

1. System initiation (see FIGS. 8a and 8b to 11a and 11b and FIG. 15.)

Operational steps:

a. Activating the overall control module 84 b. Activating the reaction and processing control module 81. Activating the motor 41 and verifying the correct initial position of the moving rack 17 (top position against the mechanical stop). Initializing the counting of steps of the motor 41. De-energizing the motor 41 and deactivating the sample homogenizer control module controller 82.

c. Activating the sample distribution control module controller 80. Activating the motor 10 and verifying the correct initial position of the rotating drum 5 (against the mechanical stop). Initializing the counting of steps of the motor 10.

2. Introducing the sample into the homogenization chamber 18

Operational steps:

a) Rotating the rotating drum 5 until the homogenization container 6 which is going to be used is vertically aligned with the hopper 4.

b) Manually introducing 250 mg of solid sample, with a particle grain size of less than 0.5 mm, into the homogenization chamber through the hopper 4.

3. Preparing the sample solution

Operational steps:

a. Rotating the rotating drum 5 (+180°) until the axis of the homogenization container 6 containing the sample is vertically aligned with the axis of the sample processing module 75 piston 24. The motor 10 is still energized so as to maintain the position of the rotating drum 5.

b. Activating the processing and reaction control module controller 81. Activating the motor 41.

c. Lowering of the moving rack 17 to the capture position (see FIGS. 9a-9b). The movement is carried out from step 0 to step 1960 (absolute values of the motor 41 step counter) at a speed of 100 steps/s.

In this position, the piston 24 and cannulas 29, 31, 28 and 29' are partially introduced into the homogenization container 18, but with no contact occurring between the elements. The accidental rotation of the drum is not possible since the container with the piston would interfere.

d. De-energizing of the motor 10.

At this time the rotating drum 5 is unlocked but its rotation is prevented by the piston 24.

e. Lowering of the moving rack 17 to the saline solution injection position (see FIGS. 10a-10b). The movement is carried out from step 1960 to step 4480 (absolute values of the motor 41 step counter) at a speed of 50 steps/s. De-energizing of the motor 41 of the moving rack at the end of travel.

In this position the saline solution cannula 28 has traversed the top cap 27a of the fluorescent marker chamber and is ready to dispense the solution. 1 mg of fluorescent marker Cy5, in solid state and adhered to the bottom and walls of the chamber, is deposited in this chamber.

The gasket 26 in turn is located above the homogenization chamber venting port, so the hermetic sealing of the chamber has not occurred.

f. Activating the reagent and solution management control module controller 82. Activating the motor 64 of the saline solution syringe until injecting 1362 µl (139 steps of the motor at 5 steps/s). De-energizing of the motor 64 upon concluding the injection.

The saline solution (0.1M $NaCO_3/NaHCO_3$) dissolves the fluorescent marker Cy5 when traversing the chamber, entraining it to the homogenization chamber 18 where the sample is located. During the injection process, the saline solution penetrates into the sensor chambers and other access conduits to the homogenization chamber. In the end, about 1200 µl of sample and marker solution are obtained in this chamber, which solution is capable of binding to the molecules carrying an amino group ($NH_2$).

g. Activating the motor 41 of the moving rack and the lowering thereof to the homogenization position. De-energizing of the motor 41.

Figure 11A:
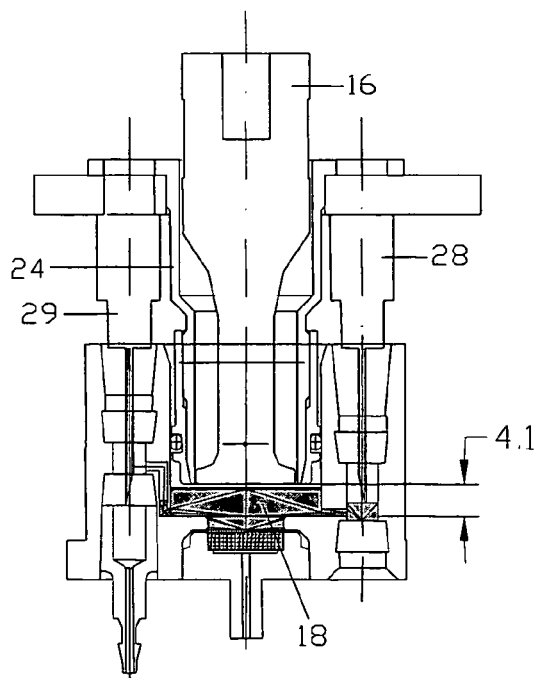
Figure 11B:
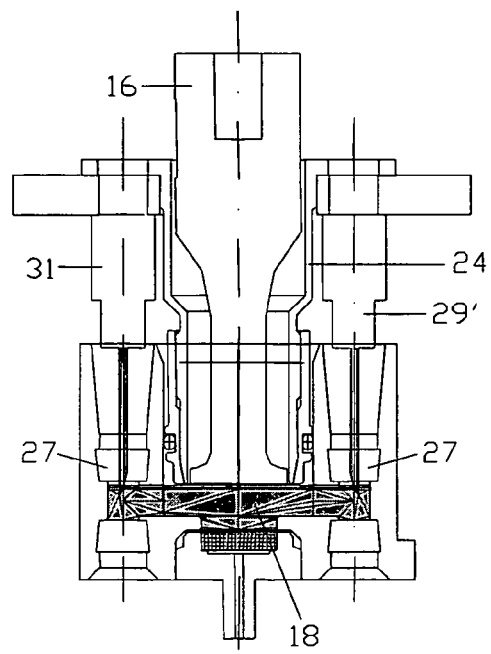
Figure 12A:
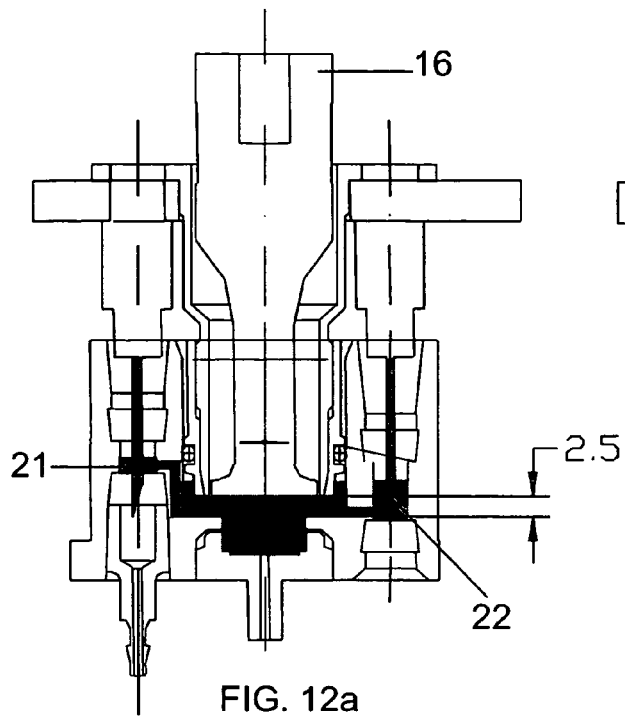
Figure 12B:
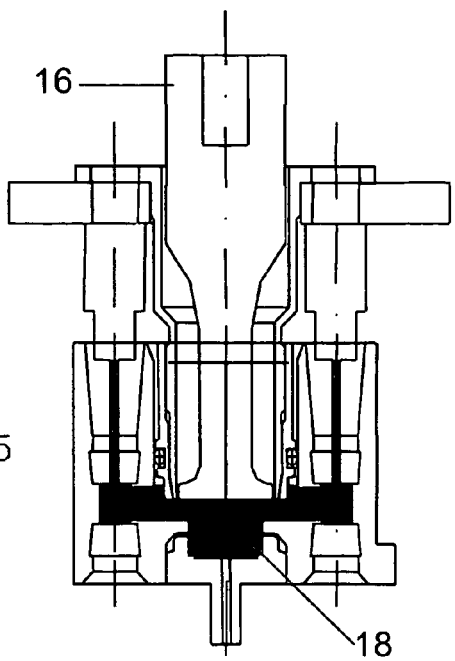
Figure 13A:
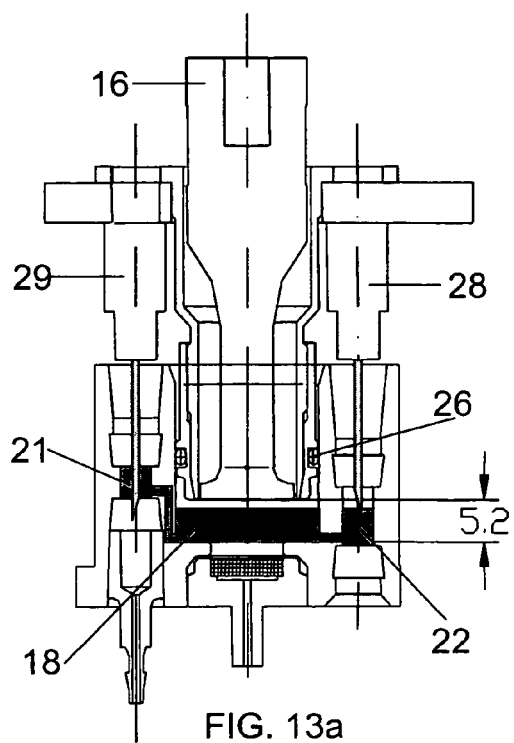
Figure 13B:
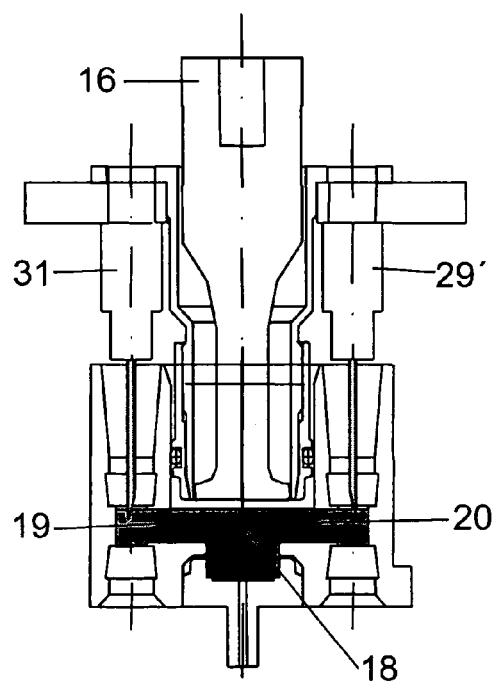

The hermetic sealing of the homogenization chamber 18 is carried out during this lowering movement of the piston 24 when the absolute step counter of motor 38 marks step 4740, approximately (see FIGS. 11a-11b). From this moment on, the homogenization chamber 18 begins to become pressurized, the overpressure increasing as the piston is lowered 24. In this position, the cannulas 29' and 31 of the pressure and temperature sensors 30 and 32, respectively, have traversed the top caps of their respective chambers and, therefore, they begin to monitor the homogenization chamber conditions. The lowering is stopped when the overpressure indicated by the sensor 30 reaches the value of 0.8 bar. The homogenization position is reached at this time (see FIGS. 12a-12b).

In this position, the PTFE membrane 41 is in contact with the sample solution, ready to be energized by the homogenization horn 16. The pressurized air existing in the chamber is retained in the cavities formed by the bushing 46 of the piston 24, close to the gasket 26.

The lowering movement is carried out in two continuous but differentiated steps: the first step, to the hermetic seal of the chamber, is carried out between absolute steps 4480 and 4740 of the motor 41, at a speed of 10 steps/s, and the second step, to the homogenization position, is slowly carried out between absolute steps 4740 and 5080 (the final step is approximate since control is carried out with the pressure sensor) of the motor 41 at a speed of 5 steps/s.

4. Sample solution homogenization

Operational steps:

a. Activating the sample homogenizer control module controller 82. Activating the sample homogenizer module piezoelectric system to homogenize the sample.

During the sample homogenization process, the converter 49 transforms the high frequency electrical power (40 kHz), supplied by the sample homogenizer control module 82, into longitudinal vibrations that are amplified through the free end of the horn 16. The horn vibrations in turn generate pressure waves in the processed sample solution, causing cavitation in the solution, homogenizing the sample. The intensity of the cavitation, and therefore the degree of homogenization of the mixture, can be regulated by choosing the amplitude of the vibrations, being able to cover a range from gentle homogenization for low amplitudes to the breaking of cells for high amplitude levels.

During the homogenization process the sample process temperature increases as a result of the energy provided thereto by the homogenizer. The temperature increase generates an increase in the overpressure in the chamber. If the process is prolonged over time, the overpressure in the homogenization chamber 18 matches the overpressure of the reaction chamber, causing a spontaneous and uncontrolled flow of sample solution to said chamber. On the other hand, the increased temperature of the solution can cause irreversible damage to the cells. These potential risks are prevented by controlling the homogenization process by means of two parameters:

The solution temperature, monitored by the temperature sensor 32, the upper limit of which must not exceed the pre-established critical temperature.

The overpressure in the homogenization chamber, monitored by the pressure sensor 30, the useful range of which for homogenization must be between 0.8÷1.0 bar.

Both parameters are closely related to other parameters, such as:

The intensity of homogenizer energizing, the value of which, predefined according to the desired degree of homogenization, is related with the ultrasonic vibration amplitude. This amplitude is preselected in the sample homogenizer control module controller 82. The useful range can be considered between 10% and 100% of the amplitude.

The homogenizer energizing time, which is related with the chosen energizing temperature: the greater the intensity, the more quickly the temperature and pressure increase and therefore the energizing interval must be reduced so as to not exceed the upper pressure and temperature limits.

The nature of the sample, room temperature, etc.

A homogenization mode capable of causing the breaking and lysis of possible cells present in the sample solution consists in intermittently activating the sample homogenizer module 76 at an energizing amplitude of 80%, in energizing intervals not exceeding 20 seconds, limited by the mentioned pressure and temperature limits. The waiting time between the intervals is defined by the pressure drop, generated by the cooling of the sample, resuming the energizing when the overpressure reaches the value of 0.8 bar.

b) 30 minute wait to facilitate the reaction of the Cy5 marker with the sample molecules.

5. Fluorescent marker blocking
Operational steps:
a. Activating the motor 41 of the moving rack and raising it to the blocker injection position (see FIGS. 13a-13b). De-energizing the motor 41.

This raising movement is carried out continuously between absolute steps 5080 (approximate) and 4500 of the motor 41 at a speed of 20 steps/second. The overpressure in the homogenization chamber decreases as the piston 24 is raised, being reduced to 0 bar when the gasket 26 surpasses the chamber venting port (absolute step 4560 of the motor 38). At the end of this step the cannula 29 is located inside the blocker chamber 21, ready to dispense the BSA solution.

b. Activating the reagent and solution management control module controller 77. Activating the motor 64 of the BSA blocker solution syringe 10 until injecting 343 μl (35 steps of the motor at 5 steps/second). De-energizing of the motor 64 upon concluding the injection.

The blocker syringe contains a saline solution with a 10% concentration of the BSA blocker. Therefore 34 mg of BSA blocker dissolved in the 343 μl of saline solution injected through the cannula 25 are added. The blocker binds to the fluorescent marker excess that has not reacted with the sample molecules. This allows decreasing the background in the image that is finally obtained because the non-specific binding of the free marker to the antibodies is prevented.

c. Activating the motor 41 of the moving rack and lowering it to the sample solution stirring position. De-energizing the motor 41.

As in operational step 3 g), the hermetic sealing of the homogenization chamber is carried out during the lowering movement of the piston 24 when the absolute step counter of the motor 41 marks step 4740 approximately. From this moment on, the homogenization chamber begins to become pressurized, increasing the overpressure as the piston is lowered 24. The lowering is stopped when the overpressure indicated by the sensor 30 reaches the value of 0.8 bar (approximately at step 4980 of the motor 41). The lowering movement is carried out in two continuous steps: the first one, between absolute steps 4500 and 4740 of the motor 41, at a speed of 20 steps/second, and the second one until reaching an overpressure of 0.8 bar at a speed of 5 steps/second.

d. Activating the sample homogenizer control module controller 82. Activating the sample homogenizer module 76 piezoelectric system so as to gently stir the sample.

This stirring has the object of homogenizing the sample solution plus BSA blocker mixture. It is carried out at a low energizing level (amplitude of 20%) for a short interval of about 5 seconds.

e. 30 minute wait to facilitate the reaction of the blocker with the marker excess.

6. Injecting the sample in the reaction chamber 18
Operational steps:
a. Activating the motor 41 of the moving rack and lowering it to the opening position of the non-return valve 37.

The opening of the non-return valve occurs when the overpressure in the homogenization chamber is slightly greater than the overpressure in the circuit of the reaction module 86, i.e. when it reaches an approximate value of 1.3 bar. This situation occurs around step 5040 of the motor 41 b. Introducing the first sample injection in the reaction chamber by means of the lowering of the moving rack.

In the first injection, the motor 41 is lowered 210 (relative) steps at a speed of 5 steps/second, so that the sample reaches the reaction chamber, traversing the filter 33, the filter holder 34, the non-return valve 37 and all the access conduits, as well as the reaction chamber itself, where the detecting substance microarray is located.

The filter 33 placed under the homogenization chamber 18 prevents particles exceeding 20 μm from entering the reaction module. The reaction chamber volume is about 28 μl. The useful detecting substance microarray dimension is 8×8 mm.

b. De-energizing the motor 41.

c. 20 minute wait to facilitate the reaction of the homogenized sample substances with the reaction chamber detecting substances.

e. Introducing the second sample injection into the reaction chamber by means of the lowering of the moving rack.

Several volumes of the sample are made to sequentially pass over the same microarray. In the second and successive injections, the motor 41 is lowered 20 (relative) steps at a speed of 5 steps/second so that the reaction chamber is occupied by a new sample. The sample assayed in the previous step passes to the waste deposit 46 where it is stored.

f. Repeating steps c), d) and e) as many times as necessary until reaching the final position (see FIGS. 14a-14b). This occurs around step 5500 of the motor 41.

As new sample injections are introduced in the reaction chamber, the overpressure of the circuit increases until reaching an approximate value of 1.7 bar at the end of the sample injection process.

g. De-energizing the motor 41.

7. Washing the reaction chamber

Operational steps:

a. Activating the reagent and solution management control module controller 82. Activating the motor 64 of the BSA blocker solution syringe 60 until injecting 1000 μl (160 steps of the motor at 5 steps/second). De-energizing the motor 64 upon concluding the injection.

Figures 14A, 14B:
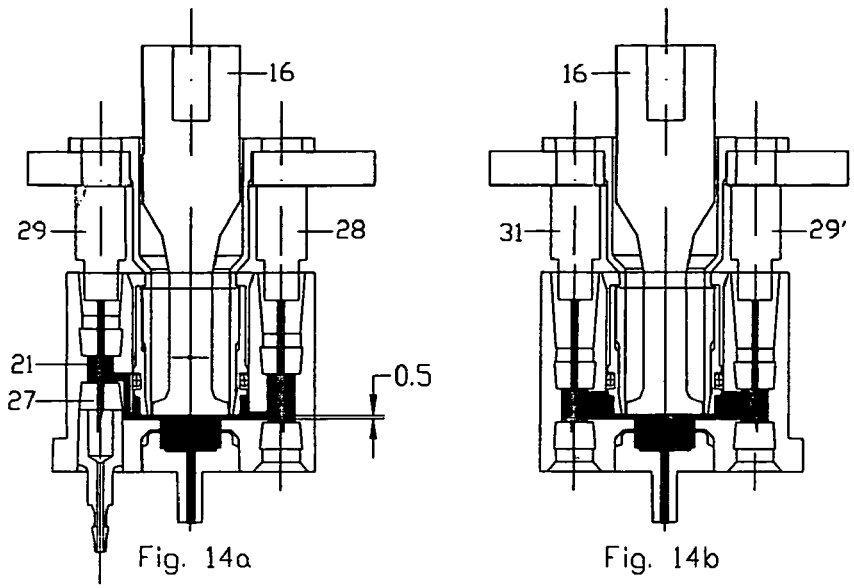

In the final position shown in FIGS. 14a-14b, the cannula 29 has traversed the bottom cap 27 of the blocker chamber 21, penetrating the reaction module 86 washing conduit 53. This allows for injecting the 10% BSA blocker solution which is also used as a reaction chamber washing solution.

The washing allows removing the marker and sample excess existing in the reaction chamber. The washing solution is finally stored in the waste deposit 57, increasing the overpressure in the reaction module up to about 2.5 bar. This overpressure is not monitored by the sensor 30 because the non-return valve 37 acts as a pressure barrier.

8. Activating the fluorescent marker and detecting the fluorescence.

Operational steps:

a. Activating the data reader control module controller 83.

b. Energizing the Cy5 fluorescent marker by means of the laser diode and simultaneously detecting the electromagnetic radiation emitted by the fluorescent molecules by means of the CCD sensor.

The Cy5 marker used has maximum absorption at 649 nm and maximum emission at 670 nm.

c. Recording the CCD sensor image on a disc.

9. Restarting the apparatus.

Operational steps:

a. Activating the motor 41 of the moving rack and raising it up to the homogenization container capture position (see FIGS. 9a-9b).

This raising movement is continuously carried out up to step 1960 of the motor 41 at a speed of 50 steps/second.

b. Energizing the motor 10 of the rotating drum.

c. Activating the motor 41 of the moving rack and raising it to the initial position (see FIGS. 8a-8b). De-energizing the motor 41.

This raising movement is continuously carried out up to step 0 of the motor 41 at a speed of 50 steps/second.

d. Rotating the rotating drum to its initial position

In this position the apparatus is ready to process a new sample.

FIGS. 16 and 17 show an embodiment variant of the apparatus in which the same references are used for designing matching or equivalent objects.

In this embodiment, the sample processing module containers 6 are assembled on a rotating drum with a horizontal shaft which, as in the previous case, is actuated by a geared motor 10 with an angular potentiometer 10'.

The chambers 6 are provided with a side loading opening 90 provided with closing means for receiving samples, which are fed through a hopper 4.

As in the previously described embodiment, in the case of FIGS. 16 and 17 the homogenizer module includes a piezoelectric device including a converter 15 and a horn 16, all this being assembled on a rack 17, the movement of which moves the closing means and through which, and by means of the actuation of the piezoelectric device, sample homogenization occurs. The rack 17 is assembled on guides 92 along which it can move, on one side of the rotating drum and with no rotational ability, by means of a linear actuator 93 with a linear potentiometer 15'.

In all other respects, in this embodiment the apparatus corresponds with the constitution described in reference to FIGS. 4 to 14, including a laser 66, a data reading camera 67, etc. It may further have a cooling module 94, a solution deposit 95 and solution pump 96.

The entire assembly shown in FIGS. 16 and 17 would be assembled in a cage structure where the hopper 4, the reagent management module, the data reading module and the communication and control modules would also be assembled.

The invention claimed is:

1. An apparatus for detecting substances or analytes from the analysis of one or several samples, comprising:
   a sample homogenizer module acting on a sample contained in a container to produce the homogenization thereof;
   a sample processing module including a series of independent containers, each one of which is intended for receiving one of the samples to be analyzed;
   a reaction module including a series of reaction chambers, as many as there are containers included in the sample processing module, each one of which is communicated with one of said containers through a controlled passage conduit and includes a sensor system for detecting substances;
   a sample distribution module including a hopper or funnel with a fixed position in which samples to be analyzed are poured, the sample distribution module being responsible for adding or distributing samples to a chosen processing module container or containers and for bringing samples contained in a chosen container into contact with the sample homogenizer module and is fed by sample injectors from samples stored in multiwell plates;
   a reagent and solution management module storing and dispensing the reagents and solutions necessary in each process step;
   a data reading module through which the reactions occurring in the reaction chambers are detected and the detected signals are processed; and
   an overall controller supervising the process and each of the sample homogenizer module, sample processing module, reaction module, sample distribution module, reagent and solution management module, and data reading module.

2. An apparatus according to claim 1, wherein the sample distribution module includes a rotating drum in which the sample processing module containers are assembled and are rotational about a vertical or horizontal shaft, which drum is capable of always placing a chosen container in communication with the hopper or funnel and, subsequently, with a sample processing module piston.

3. An apparatus according to claim 1, wherein the reaction module chambers are assembled in a rotating drum of the sample distribution module.

4. An apparatus according to claim 1, wherein the sample processing module further comprises means for closing the container housing the samples to be analyzed during the processing of said sample, which means consist of a piston assembled in a rack located above the rotating drum and under which the different containers can be placed by means of the rotation of said drum, the rack being movable in the longitudinal direction between a top open position and another bottom closed position of the container placed immediately underneath.

5. An apparatus according to claim 4, wherein the sample processing module rack is assembled on the sample distribution module movement shaft, on one of the sides of said module, without rotational ability but with the ability to slide thereon between end positions determined by a sensor.

6. An apparatus according to claim 1, wherein the sample processing module further comprises means for closing the container housing the samples to be analyzed during the processing of said samples, which means consist of a piston assembled on a rack placed on one side of the rotating drum and opposite which the different containers may be arranged, placed on the other side of the drum as a result of the rotation of said drum, the rack being moveable between an open position and a closed position.

7. An apparatus according to claim 6, wherein the rack is assembled on guides along which it can move, on one side of the rotating drum and with no rotational ability, by means of a linear actuator with a linear potentiometer.

8. An apparatus according to claim 6, wherein said piston has a tubular structure and the sample homogenization device acts through it.

9. An apparatus according to claim 1, wherein each one of the sample processing module containers further comprises means for the closing thereof, which means consist of a piston or valve assembled in each container and actuated by the movement of the homogenization module moving rack.

10. An apparatus according to claim 1, wherein each sample processing module container includes one or more main homogenization chambers and one or more independent secondary chambers intended for containing the reagents, intercommunicated with the main chamber, said main chamber being open so as to receive the sample to be analyzed and the closing means, and having a bottom port with a filter and a flow valve, through which the homogenized sample is injected into the reaction module.

11. An apparatus according to claim 10, wherein the wall of the main chamber has a venting port located above the intercommunication ports with the secondary chambers, determining the moment of the hermetic sealing of said chamber by a piston when said port is surpassed by a gasket of the piston, said piston being movable inside the main chamber from the hermetic sealing position so as to cause the pressure inside said chamber to increase.

12. An apparatus according to claim 11, wherein the sample introduction into the main chamber is carried out through the venting port.

13. An apparatus according to claim 10, wherein the secondary chambers are closed at the top and bottom parts by means of caps through which cannulas belonging to the reagent management module for injecting reagents or solutions, or which carry pressure or temperature sensors, or sensors for other physicochemical parameters, can be introduced.

14. An apparatus according to claim 10, wherein the flow valve located between the main chamber of each sample processing module container and the reaction module chamber consists of a non-return valve, the closing of which occurs when an overpressure is created in the reaction module chamber with respect to the sample processing module main chamber.

15. An apparatus according to claim 1, wherein a longitudinally moving rack includes the sample homogenization means, which consist of a device with thermal or mechanical action or a wave generator capable of acting on the samples.

16. An apparatus according to claim 1, wherein the reaction module comprises, for each sample processing module container, a body defining an internal reaction chamber having an inlet connected to a main chamber of said container through a non-return valve, an inlet connected to a secondary chamber of said container through which a washing solution is injected, and a solution outlet to a waste deposit; one of the walls of said chamber carrying the sensor system configured for detecting substances present in the homogenized solution or suspension injected in the chamber.

17. An apparatus according to claim 1, wherein the reagent and solution management module comprises at least one motorized syringe responsible for storing and dispensing fluids which is accompanied by a linear actuator actuating the syringe plunger rod, a position sensor to obtain the position of the plunger, a non-return valve and an injection cannula fixed to the sample processing module moving frame.

18. An apparatus according to claim 17, wherein it comprises a series of reagent and solution deposits, there being the same number of deposits as different reagents and solutions are needed, and at least one pumping device capable of aspirating the fluids from the different deposits and dispensing them into the homogenization or reaction chamber.

19. An apparatus according to claim 1, wherein the reaction module is made up of a receptacle to house a biosensor that includes a system of stirring or moving the liquid sample so as to improve the working of said biosensor, which has at least one inlet port for the sample coming from the sample processing module container, at least one inlet port for additional liquid solutions, and at least one outlet port for the different solutions and pipes or conduits that are necessary and are connected by a conduit where a pumping system is arranged which allows recirculating the sample on the biosensor.

20. An apparatus according to claim 19, wherein said biosensor is formed by detecting substances immobilized on a solid support in the form of a microarray or biochip, distributed in flow channels or chambers.

21. An apparatus according to claim 1, wherein the data reading module comprises a reaction detector including a light source that may be monochromatic or not, for energizing the biosensor and a CCD camera coupled to filters to detect only the appropriate radiation.

22. An apparatus according to claim 21, wherein the monochromatic light is guided by means of a waveguide in which the biosensor is located, which biosensor is energized as a result of the evanescent modes forming on the outer surface of said guide.

23. An apparatus according to claim 1, further comprising a cage-shaped structure assembled in which there is a central vertical column, which defines the rotation shaft of a sample distribution module rotating drum, and along which column the sample processing module rack can slide, the sample acquisition module hopper or funnel, the reagent management module and the data reading module being assembled in said cage-shaped structure.

24. An apparatus according to claim 1, further comprising a cage-shaped structure assembled in which, according to a horizontal shaft, is the sample distribution module rotating drum and parallel to said shaft, the guides through which the sample processing module rack slides, the sample acquisition module hopper or funnel, the reagent management module, the data reading module and the communication and control modules also being assembled in said cage-shaped structure.

* * * * *

UNITED STATES PATENT AND TRADEMARK OFFICE
CERTIFICATE OF CORRECTION

PATENT NO. : 8,097,209 B2
APPLICATION NO. : 10/558936
DATED : January 17, 2012
INVENTOR(S) : Gómez-Elvira Rodríguez et al.

Page 1 of 1

It is certified that error appears in the above-identified patent and that said Letters Patent is hereby corrected as shown below:

In the Claims:

Col. 28, Line 51: "the reagents" should read --reagents--

Signed and Sealed this
Fourth Day of June, 2013

Teresa Stanek Rea
*Acting Director of the United States Patent and Trademark Office*